(12) United States Patent
Chen et al.

(10) Patent No.: US 9,132,208 B2
(45) Date of Patent: Sep. 15, 2015

(54) COMPOSITION FOR A TISSUE REPAIR IMPLANT AND METHODS OF MAKING THE SAME

(75) Inventors: Silvia S. Chen, Virginia Beach, VA (US); Jingsong Chen, Virginia Beach, VA (US); Lloyd Wolfinbarger, Jr., Norfolk, VA (US)

(73) Assignee: LifeNet Health, Virginia Beach, VA (US)

( * ) Notice: Subject to any disclaimer, the term of this patent is extended or adjusted under 35 U.S.C. 154(b) by 555 days.

(21) Appl. No.: 12/188,127

(22) Filed: Aug. 7, 2008

(65) Prior Publication Data
US 2010/0036503 A1   Feb. 11, 2010

(51) Int. Cl.
| | |
|---|---|
| *A01N 1/00* | (2006.01) |
| *A61L 27/36* | (2006.01) |
| *A61L 27/38* | (2006.01) |
| *A61L 27/56* | (2006.01) |
| *A61F 2/28* | (2006.01) |
| *A61F 2/30* | (2006.01) |

(52) U.S. Cl.
CPC ......... *A61L 27/3683* (2013.01); *A61L 27/3604* (2013.01); *A61L 27/3608* (2013.01); *A61L 27/38* (2013.01); *A61L 27/56* (2013.01); *A61F 2/28* (2013.01); *A61F 2/30756* (2013.01); *A61F 2310/00359* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 4,522,753 A | 6/1985 | Yannas | |
| 4,808,570 A | 2/1989 | Michaeli | |
| 5,053,049 A | 10/1991 | Campbell | |
| 5,350,583 A | 9/1994 | Yoshizato | |
| 5,531,791 A * | 7/1996 | Wolfinbarger, Jr. | 623/23.63 |
| 5,556,430 A | 9/1996 | Gendler | |
| 5,718,916 A | 2/1998 | Scherr | |
| 5,776,193 A | 7/1998 | Kwan | |
| 5,888,987 A | 3/1999 | Haynes | |
| 6,080,194 A | 6/2000 | Pachence | |
| 6,187,047 B1 | 2/2001 | Kwan | |
| 6,306,169 B1 | 10/2001 | Lee | |
| 6,309,659 B1 | 10/2001 | Clokie | |
| 6,309,670 B1 | 10/2001 | Heidaran | |
| 6,311,690 B1 | 11/2001 | Jefferies | |
| 6,326,018 B1 | 12/2001 | Gertzman | |
| 6,334,968 B1 | 1/2002 | Shapiro | |
| 6,447,701 B1 | 9/2002 | Heschel | |
| 6,793,675 B2 | 9/2004 | Shapiro | |
| 6,808,585 B2 | 10/2004 | Boyce | |
| 6,852,330 B2 | 2/2005 | Bowman | |
| 6,884,428 B2 | 4/2005 | Binette | |
| 7,001,551 B2 | 2/2006 | Meredith | |
| 7,045,141 B2 | 5/2006 | Merboth | |
| 7,128,929 B1 | 10/2006 | Scherr | |
| 7,131,994 B2 | 11/2006 | Mills | |
| 7,132,110 B2 | 11/2006 | Kay | |
| 7,498,040 B2 | 3/2009 | Masinaei | |
| 7,498,041 B2 | 3/2009 | Masinaei | |
| 7,824,701 B2 * | 11/2010 | Binette et al. | 424/423 |
| 2002/0082694 A1 | 6/2002 | McKay | |
| 2003/0003157 A1 | 1/2003 | Ohan | |
| 2004/0097612 A1 | 5/2004 | Rosenberg | |
| 2004/0230309 A1 | 11/2004 | DiMauro | |
| 2006/0067967 A1 | 3/2006 | Bowman | |
| 2006/0159663 A1 | 7/2006 | Lu | |
| 2006/0204544 A1 | 9/2006 | Sunwoo | |
| 2007/0065943 A1 | 3/2007 | Smith | |

(Continued)

FOREIGN PATENT DOCUMENTS

| | | | |
|---|---|---|---|
| WO | 99/19005 A1 | 4/1999 | |
| WO | 9919005 A1 | 4/1999 | |

(Continued)

OTHER PUBLICATIONS

Lee CS, et al., Integration of layered chondrocyte-seeded alginate hydrogel scaffolds, Biomaterials, Jul. 2007;28(19):2987-93. Epub Mar. 5, 2007.
van Susante JL, et al., Culture of chondrocytes in alginate and collagen carrier gels, Acta Orthop Scand, Dec. 1995;66(6):549-56.
Marijnissen WJ, et al., Tissue-engineered cartilage using serially passaged articular chondrocytes, Chondrocytes in alginate, combined in vivo with a synthetic (E210) or biologic biodegradable carrier (DBM), Biomaterials, Mar. 2000;21(6):571-80.
Pound JC, et al., An ex vivo model for chondrogenesis and osteogenesis, Biomaterials, Jun. 2007;28(18):2839-49. Epub Mar. 23, 2007.

(Continued)

*Primary Examiner* — Kade Ariani
(74) *Attorney, Agent, or Firm* — Morgan, Lewis & Bockius LLP

(57) ABSTRACT

The invention is directed to a process for making a tissue repair implant having a porous sponge-like structure to repair bone, cartilage, or soft tissue defects by producing a connective tissue homogenate from one or more connective tissues; mixing the connective tissue homogenate with a carrier solution to produce a connective tissue carrier; optionally mixing one or more natural or synthetic bone fragments with said connective tissue carrier to produce a tissue repair mixture; freezing or freeze-drying the tissue repair mixture to produce a porous sponge-like structure and create a three-dimensional framework to entrap the natural or synthetic bone fragments, treating the frozen or freeze-dried porous sponge-like structure with one or more treatment solutions to produce a stabilized porous sponge-like structure. A crudely fragmented connective tissue from one or more connective tissues is optionally mixed with the tissue repair mixture before freezing or freeze-drying. The tissue repair implant having a porous sponge-like structure is optionally combined with one or more bioactive supplements or one or more agents that have bioactive supplement binding site(s) to increase the affinity of growth factors, differentiation factor, cytokines, or anti-inflammatory agents to the tissue repair implant. The invention is further directed toward applying such tissue repair implant for tissue repair.

67 Claims, 6 Drawing Sheets

(56) References Cited

U.S. PATENT DOCUMENTS

| | | | |
|---|---|---|---|
| 2007/0083270 A1 | 4/2007 | Masinaei | |
| 2007/0093912 A1 | 4/2007 | Borden | |
| 2007/0254041 A1* | 11/2007 | Drapeau et al. | 424/550 |
| 2008/0147197 A1 | 6/2008 | McKay | |

FOREIGN PATENT DOCUMENTS

| | | |
|---|---|---|
| WO | 2004/017915 A2 | 3/2004 |
| WO | 2004017915 A2 | 3/2004 |
| WO | WO 2004/045372 | 6/2004 |
| WO | WO 2006027622 A2 * | 3/2006 |
| WO | WO 2006/076712 | 7/2006 |

OTHER PUBLICATIONS

Cho SH, et al., Fabrication and characterization of porous alginate/polyvinyl alcohol hybrid scaffolds for 3D cell culture, J Biomater Sci Polym Ed., 2005; 16(8):933-47.

Shapiro L and Cohen S, Novel alginate sponges for cell culture and transplantation, Biomaterials, Apr. 1997;18(8):583-90.

Glicklis R, et al., Hepatocyte behavior within three-dimensional porous alginate scaffolds, Biotechnol Bioeng, Feb. 5, 2000;67(3):344-53.

Avella M, et al., Addition of glycerol plasticizer to seaweeds derived alginates: Influence of microstructure on chemical—physical properties, Carbohydrate Polymers 69 (2007) 503-511.

Pongjanyakul T and Puttipipatkhachom S, Aliginate-magnesium aluminum silicate films: Effect of plasticizers on film properties, drug permeation and drug release from coated tablets, Int J Pharm., Mar. 21, 2007;333(1-2):34-44. Epub Sep. 30, 2006.

Ohta M, et al., Novel heparin/alginate gel combined with basic fibroblast growth factor promotes nerve regeneration in rat sciatic nerve, J Biomed Mater Res A, Dec. 15, 2004;71(4):661-8.

Lee KW, et al., Sustained release of vascular endothelial growth factor from calcium-induced alginate hydrogels reinforced by heparin and chitosan, Transplant Proc, Oct. 2004;36(8):2464-5.

Liao IC, et al., Controlled release from fibers of polyelectrolyte complexes, J Control Release, May 18, 2005;104(2):347-58. Epub Apr. 7, 2005.

Extended European Search Report issued in a related European Application No. 09805294.7, dated Dec. 11, 2013.

* cited by examiner

COMPOSITION FOR A TISSUE REPAIR IMPLANT AND METHODS OF MAKING THE SAME

FIELD OF THE INVENTION

The present invention is related to a tissue repair implant having a porous sponge-like structure and to methods of preparing such an implant. The present invention is also related to methods of using the implant to repair defective tissues.

BACKGROUND OF THE INVENTION

The ability to promote tissue regrowth in vivo can facilitate wound healing and post-surgical recovery of patients who have suffered tissue damage or destruction. The need for such methods and compositions is readily apparent, when considering that in 1999, approximately 500,000 bone graft procedures were performed in the United States alone. Ideal bone graft materials for use in such procedures possess characteristics necessary to new bone growth, namely osteoconductivity and osteoinductivity.

Osteoconductivity refers to a graft's ability to support the attachment of new osteoblasts and osteoprogenitor cells. The osteoconductive components of a graft provide an interconnected structure through which new cells can migrate and new blood vessels can form. Osteoinductivity refers to the ability of a graft to induce nondifferentiated stem cells or osteoprogenitor cells to differentiate into osteoblasts.

In 1998, 9 of 10 bone graft procedures performed in the United States involved the use of either autograft or allograft bone tissue. Despite the benefits of autografts and allografts, the limitations of each have necessitated the pursuit of alternative graft materials. Using basic criteria necessary to a successful graft (e.g., osteoconduction and osteoinduction), investigators have developed several bone graft substitutes. These can contain a variety of materials, including natural and synthetic polymers, ceramics, and composites; and in some instances, production of bone graft substitutes can involve biotechnological strategies (i.e., factor- and or cell-based strategies).

Osteoinductive substances found in some bone graft substitutes are demineralized bone particles and or powder. Contained in the extracellular matrix of bone tissue is a full cocktail of bone growth factors, proteins, and other bioactive materials necessary for osteoinduction and, ultimately, successful bone healing. To capitalize on this cocktail of proteins, bone tissue can be demineralized, leaving the osteoinductive agents in the demineralized bone matrix (DBM). Such osteoinductive DBM can be incorporated into a number of different bone graft substitutes.

While a number of different materials thought to enhance osteoconductivity (i.e., purified or partially purified polymers) have been used in DBM bone graft substitutes; new, more easily prepared, osteoconductive/structural materials for combining with DBM to produce a bone graft substitute are desirable.

SUMMARY OF THE INVENTION

The present invention provides a biologically functional tissue repair implant having a stable porous sponge-like structure. In one embodiment, the functionally active tissue repair implant of the present invention comprises a uniform composition containing a connective tissue homogenate and a carrier that are evenly distributed to form a three-dimensional framework. The tissue repair implant of the present invention may also consist essentially of evenly distributed connective tissue homogenate and carrier in a three-dimensional framework. In another embodiment, the functionally active tissue repair implant comprises an uniform composition further containing bone fragments interspersed in the connective tissue homogenate and carrier framework. The bone fragments are distributed throughout the framework. The tissue repair implant of the present invention may consist essentially of evenly distributed connective tissue homogenate, carrier, and bone fragments in a three-dimensional framework.

The tissue repair implant of the present invention may be preshaped, elastic, resilient, and insoluble in water. The implant will maintain its shape in a dry or a wet state. In its dry state, the implant will quickly absorb fluid because it is porous. For example, in its wet state, the implant will maintain its porosity, cohesiveness, and integrity.

The connective tissue homogenate may contain one or more connective tissues. The bone fragments may be natural or synthetic bone fragments.

The present invention also discloses methods for producing a biologically functional tissue repair implant having a stable porous sponge-like structure. In one embodiment, the method comprises: (a) producing a connective tissue homogenate from one or more connective tissues; (b) mixing the connective tissue homogenate with a carrier solution to produce a connective tissue carrier; (c) mixing one or more natural or synthetic bone fragments with the connective tissue carrier to produce a tissue repair mixture; (d) freezing or freeze-drying the tissue repair mixture to produce a porous sponge-like structure and create a framework to entrap the natural or synthetic bone fragments; and (e) treating the frozen or freeze-dried porous sponge-like structure with one or more treatment solutions to produce a stabilized porous sponge-like structure. Optionally, a crudely fragmented connective tissue from one or more connective tissues may be mixed with the tissue repair mixture before freezing or freeze-drying.

In another embodiment, the method for preparing a tissue repair implant having a stable porous sponge-like structure comprises: (a) producing a connective tissue homogenate from one or more connective tissues; (b) mixing the connective tissue homogenate with a carrier solution to produce a tissue repair mixture; (c) freezing or freeze-drying the tissue repair mixture to produce a porous sponge-like structure and create a framework; and (d) treating the frozen or freeze-dried porous sponge-like structure with one or more treatment solutions to produce a stabilized porous sponge-like structure. Optionally, a crudely fragmented connective tissue from one or more connective tissues may be mixed with the tissue repair mixture before freezing or freeze-drying.

Moreover, the steps set forth above for preparing the tissue repair implant may be combined or the sequential order of the steps may be changed. As an example, the carrier solution may be added to the one or more connective tissues for making connective tissue homogenate. The carrier solution may replace the water that is added to the connective tissues to make the homogenate.

The stabilized porous sponge-like structure may be treated with a water replacing agent such as glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, or lipids. The stabilized porous sponge-like structure may also be freeze-dried and/or sterilized. Sterilization may be carried out using gamma irradiation, super critical solution, ethylene oxide, or electronic-beam.

The methods of the present invention may include combining the tissue repair implant with one or more bioactive supplements. The bioactive supplements may be growth factors, differentiation factors, cytokines, or anti-inflammatory agents. The growth or differentiation factors may be a growth factor of the FGF-family or TGF-family, IGF-1, PDGF, EGF, VEGF, HGF, PTHrP, Ihh, dexamethasone, insulin, transferrin, selenium, ITS, ascorbate, or a combination thereof. The cytokines may be GM-CSF, G-CSF, TNF-α, IL-1β, IL-4, IL-6, IL-8, IL-10, SLP1, MCP1, MIP-1α, MIP-2, IL-18, angiopoietin, KGF, endothelin, IFN-α, or IFN-β. The anti-inflammatory agents may be an IL-1αR antibody, TNF-a receptor antagonist, cyclooxygenase-2 specific inhibitors, MAP kinase inhibitors, NO synthase inhibitors, NF-κB inhibitors, or inhibitors of MMP. The tissue repair implant may also be combined with one or more agents having bioactive supplement binding sites comprising hyaluronan, heparin, heparin sulfate, keratin sulfate, dermatan sulfate, chondroitin sulfate, betaglycan, heparan sulfate proteoglycan, syndecan, biglycan, or decorin. The one or more bioactive supplement binding sites on the agents may increase the affinity of growth factors, differentiation factors, cytokines, or anti-inflammatory agents to said tissue repair implant. Accordingly, the present invention also discloses a tissue repair implant comprising one or more bioactive supplements and one or more agents having bioactive supplement binding sites.

The methods of the present invention provide a tissue repair implant having a pore size that may be larger than about 50 microns and a void volume that may be from about 10% to about 95% or from about 30 to 80%. The tissue repair implant prepared by the present invention may be in the form of rod, sheet, cube, tube, particle, sphere, ellipsoid, wedge, or ribbon.

The connective tissue homogenate used in the methods of the present invention may be made from one more connective tissues of human and/or animal origins. The connective tissue may comprise dermis, fascia, cartilage, tendon, ligament, pericardium, fat, muscle, urethra, small intestine, demineralized bone, non-demineralized bone or a combination thereof.

The connective tissue in the connective tissue homogenate used in the methods of the present invention may be cleaned and/or disinfected. The connective tissue may also be devitalized to remove cellular components. The connective tissue may be freeze dried.

In the methods of the present invention, the connective tissue homogenate may be prepared by homogenizing said connective tissue at temperature from about 15° C. to about 100° C. for a period of time of about 0.5 minutes to about 30 minutes. The homogenization may be carried out in the presence of a solution. The weight percentage of the connective tissue homogenate in the tissue repair implant may be no more than 80% in the dry state, no more than 50% in the dry state, or no more than 20% in the dry state.

The carrier solution used in the processes of the present invention may comprise one or more polysaccharides selected from the group comprising alginate, propylene glycol alginate, native or crosslinked chitosan, starch, cellulose and its derivatives (such as cellulose acetate, carboxymethyl cellulose, and methyl cellulose), xanthan gum, dextran, carrageenan, hyaluronic acid, chondroitin sulfate, locust bean gum, gum tragacanth, gum arabic, curdlan, pullulan, scleroglucan, or lower methoxylpectin. The carrier solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The carrier solution may also contain natural and or synthetic polymers such as but limited to native or modified collagen, gelatin, agarose, modified hyaluronic acid, fibrin, chitin, biotin, avidin, MATRIGEL®, HUMAN EXTRACELLULAR MATRIX®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, polylactic acid, or a combination comprising at least one of the foregoing polymers.

In one embodiment, the carrier solution used in the methods of the present invention to make the tissue repair implant may comprise bioactive supplements. The bioactive supplements may be growth factors, differentiation factors, cytokines, or anti-inflammatory agents. The growth or differentiation factors may include but are not limited to a growth factor of the FGF-family or TGF-family, IGF-1, PDGF, EGF, VEGF, HGF, PTHrP, Ihh, dexamethasone, insulin, transferrin, selenium, ITS, ascorbate, or a combination thereof. Examples of cytokines may include GM-CSF, G-CSF, TNF-α, IL-1β, IL-4, IL-6, IL-8, IL-10, SLP1, MCP1, MIP-1α, MIP-2, IL-18, angiopoietin, KGF, endothelin, IFN-α, or IFN-β. The anti-inflammatory agents may include but are not limited to an IL-1αR antibody, TNF-α receptor antagonist, cyclooxygenase-2 specific inhibitors, MAP kinase inhibitors, NO synthase inhibitors, NF-κB inhibitors, or inhibitors of MMP. The carrier solution may comprise bioactive supplements extracted from tissue selected from the group comprising demineralized bone matrix, basement membrane, or submucosa matrix. In another embodiment, the carrier solution may also comprise antioxidants selected from the group comprising sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene.

Alternatively, the carrier solution used in the methods of the present invention may comprise photoactive agents selected from the group comprising a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide-N,N9-bis(3-diazopyruvoyl)-2,29-(ethylenedioxy)bis-(ethylamine) (DPD); diazopyruvoyl (DAP); methylene blue, erythrosin, phloxime, thionine, methylene green, rose Bengal, acridine orange, xanthine dye, and thioxanthine dyes, ethyl eosin, eosin Y, or a combination comprising at least one of the foregoing photoactive groups. The photoactive agent may be activated using a UV light or a laser. The weight percentage of the carrier in the tissue repair implant may be no more than 20% in the dry state or no more than 5% in the dry state.

The natural or synthetic bone fragments materials used in the methods of the present invention to prepare the implants may comprise non-demineralized bone, partially demineralized bone, demineralized bone, ceramics, hydroxyapatite, calcium phosphate, calcium sulfate, calcium carbonate, or a combination of two or more of the above. The natural bone fragments may be from a human or an animal. The natural or synthetic bone fragments may be in the form of particles, fibers, rods, or cubes. The particles may have an average particle size of about 125 micron to about 2000 micron or an average particle size of about 250 micron to about 710 micron. The fibers may have an average width of 0.1 to 2 mm and an average width of between about 0.3 mm and about 2.5 mm. Fibers may be of varying lengths. An average length of the fiber may range from about 0.3 mm to about 100 mm. The rods may have an average width of 0.5 to 3 mm and an average length of about 1 mm to about 100 mm. The cubes may have an average volume of about 0.001 mm$^3$ to an average volume of about 1000 mm$^3$.

The demineralized bone used in the methods of the present invention may have a residual calcium content less then 8% or from about 1% to about 4%.

The weight percentage of the natural or synthetic bone fragments used in the methods of the present invention to prepare the tissue repair implant is about 0.1% to about 95% in the dry state, or about 10% to about 90% in the dry state.

The crudely fragmented connective tissue used in the methods of the present invention may be obtained from tissues that are cleaned, disinfected, optionally devitalized to remove cellular components, and optionally freeze-dried. The crudely fragmented connective tissue may be from tissues comprising fascia, cartilage, ligament, tendon, pericardium, muscle, urethra, small intestine, demineralized bone, dermis, partial demineralized bone, or non-demineralized bone.

The average diameter of the crudely fragmented connective tissue may be from about 0.01 to about 5 mm. The weight percentage of said crudely fragmented connective tissue in said tissue repair implant is about 0.25% to about 95% in the dry state, or about 0.5% to about 90% in the dry state.

In the process of the present invention, the tissue repair mixture may be placed in a mold before the freezing or freeze-drying step. The tissue repair mixture may be optionally processed under negative hydrostatic pressure before being frozen to increase porosity.

The treatment solution used in the methods of the present invention may comprise ionic, enzymatic, or chemical crosslinking agents; or photoactive agents. The treatment solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The treatment solution may comprise natural and or synthetic polymers selected from the group comprising native or modified collagen, gelatin, agarose, modified hyaluronic acid, fibrin, chitin, biotin, avidin, demineralized bone matrix, MATRIGEL®, HUMAN EXTRACELLULAR MATRIX®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, or polylactic acid, or a combination comprising at least one of the foregoing polymers.

The treatment solution used in the process of the present invention may comprise one or more bioactive supplements. The bioactive supplements may be growth factors, differentiation factors, cytokines, or anti-inflammatory agents. The treatment solution may also contain an agent having one or more bioactive supplement binding sites. The treatment solution may comprise antioxidants to protect bioactive components from oxygen-radical-induced damage.

In the methods of the present invention, one or more treating steps with one or more treatment solutions may be conducted simultaneously or sequentially to stabilize the porous sponge-like structure and further entrap the natural or synthetic bone fragments. The treatment may be carried out for a duration of about 5 minutes to about 16 hours, about 15 minutes to about 120 minutes, or about 30 minutes to about 60 minutes.

The present invention also provides a process for repairing a defect in a tissue, for example, bone, cartilage, or soft tissue. In one aspect, the process of the present invention comprises implanting the tissue repair implant having a porous sponge-like structure of the present invention into the site of defect in the tissue without rehydration to allow the tissue repair implant to absorb blood or fluid as well as autologous cells in situ. In another aspect, the process includes rehydrating the tissue repair implant having a porous sponge-like structure of the present invention with a rehydrating solution; optionally seeding vital cells on the tissue repair implant to render the tissue repair implant vital; optionally culture the cell-seeded tissue repair implant before implantation; implanting the tissue repair implant into the defect.

The rehydrating solution may contain blood or bone marrow aspirate, platelet rich plasma, enzymes, bioactive supplements, natural polymers, synthetic polymers, photoactive agents, antioxidants, crosslinking agents, antimicrobial agents, vital cells, one or more agents that have bioactive supplement binding site(s), or a mixture of two or more of the above. The vital cells may be one or more than one type of cells from autologous or allograft bone marrow aspirate; stromal cells from bone marrow, stromal cells from fat, synovium, periosteum, perichondrium, muscle, dermis, umbilical cord blood, and Warton's jelly; or pericytes.

DESCRIPTION OF THE INVENTION

General Description of the Invention

Figure 1:
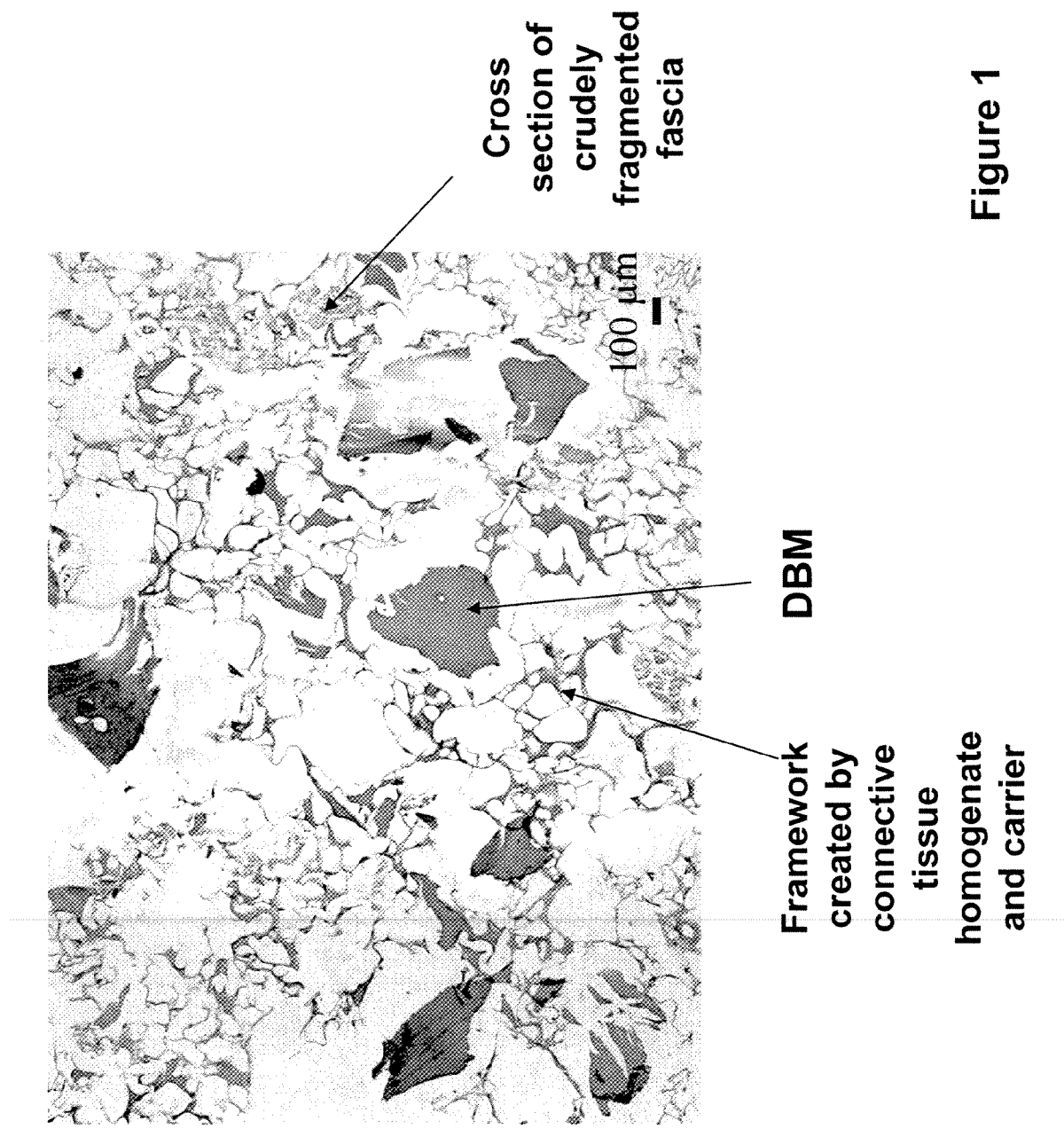
FIG. 1 shows H&E staining of a porous sponge-like structure containing DBM comprised of a framework created by connective tissue homogenate and alginate, crudely fragmented fascia, and DBM particles. The porous sponge-like structure was freeze-dried and treated with CaCl$_2$.

The invention discloses a biologically functional tissue repair implant having a porous sponge-like structure useful for repairing defects in tissues. The tissues may be bone tissues, cartilage, or soft tissues. Examples of soft tissues may include tendon, ligament, dermis, and rotator cuff.

The invention also provides processes for making a tissue repair implant having a porous sponge-like structure to repair bone, cartilage, or soft tissue defects by producing a connective tissue homogenate from one or more connective tissues; mixing the connective tissue homogenate with a carrier solution to produce a connective tissue carrier; optionally mixing one or more natural or synthetic bone fragments with said connective tissue carrier to produce a tissue repair mixture; freezing or freeze-drying the tissue repair mixture to produce a porous sponge-like structure and create a framework to entrap the natural or synthetic bone fragments; treating the frozen or freeze-dried porous sponge-like structure with one or more treatment to produce a stabilized porous sponge-like structure. A crudely fragmented connective tissue from one or more connective tissues is optionally mixed with the tissue repair mixture before freezing or freeze drying. The tissue repair implant having a porous sponge-like structure is optionally combined with one or more bioactive supplement or one or more agents that have bioactive supplement binding site(s) to increase the affinity of growth factors, differentiation factors, cytokines, or anti-inflammatory agents to the tissue repair implant. The invention is further directed toward applying such tissue repair implant for tissue repair.

The invention also relates to a process for repairing a defect in a human or animal by implanting the tissue repair implant having a porous sponge-like structure into a defect without rehydration to allow the tissue repair implant to absorb blood or fluid as well as autologous cells in situ. Alternatively, implantation of a tissue repair implant into a human or animal can be conducted by re-hydrating the tissue repair implant with a rehydrating solution; optionally seeding vital cells on the tissue repair implant to render the tissue repair implant vital; optionally culture the cell-seeded tissue repair implant before implantation; and implanting the tissue repair implant into the defect.

Moreover, the invention is directed to producing tissue repair implants having a porous sponge-like structure using a connective tissue homogenate from one or more connective tissues, a carrier solution, and with or without one or more natural or synthetic bone fragments for tissue repair. The invention relates to a process for making a porous sponge-like structure and stabilizing the porous sponge-like structure through one or more freeze drying cycles and one or more treating steps using one or more treatment solutions.

In the present application, the term "connective tissue" refers to mesodermally and endodermally derived tissue that may be more or less specialized, and that is, at least in part, made up of fibers. Most of the connective tissues contemplated in the present invention are less specialized tissues that are rich in extracellular matrix (i.e., collagen, proteoglycan, among others), and that surround other more highly ordered tissues and organs. A relatively, more specialized tissue contemplated in the present invention is cartilage. Varieties of connective tissue that may be used in the present invention include but not limited to adipose; loose connective tissue; dense, regular, irregular, or elastic connective tissue; white fibrous connective tissue; and cartilage. Connective tissue may be classified according to concentration of fibers as loose (areolar) and dense, the latter having more abundant fibers than the former. Connective tissues may be obtained from vertebrates. In some embodiments, the tissues may have human, bovine, equine, porcine, ovine, caprine, or piscene origins, among others. Connective tissues may also be the product of biotechnological methods, for example, tissue engineered connective tissues produced using cell culture methods.

Specific examples of connective tissues that may be used in certain embodiments of the present invention include but are not limited by at least, fascia, dermis tendons, ligaments, pericardium, urethra, small intestine, muscle, bone, dermis, or cartilage. Examples of different types of fascia that may be used in certain embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. "Crudely fragmented connective tissue" refers to connective tissue that has been sliced, ground, carved, chipped, chopped, minced, cut, dissected, rent, ripped, sectioned, snipped, diced, shaved, comminuted, or trimmed into fragments. Such fragmented connective tissue may have an average diameter greater than about 50 microns and less than about 0.5 cm, for example, having cut dimensions of approximately 0.5×0.5 cm, and a thickness appropriate to the tissue being crudely fragmented. In some embodiments, the crude fragments may not be of uniform size. "Homogenized connective tissue" or "connective tissue homogenate" contains connective tissue that has been reduced to particles that are uniformly small and evenly distributed. Homogenized connective tissue may optionally include at least one of water, aqueous solutions, or water miscible polar organic solvents, in addition to the particles. The homogenized connective tissues used in methods of the present invention include particles having an average diameter of less than about 50 microns. In some embodiments, the homogenized connective tissue may be prepared by shear-induced shredding of a composition comprising connective tissue, and optionally, at least one of water, an aqueous solution and a water miscible polar organic solvent. A conventional blender may be used in preparing the homogenized connective tissue, in certain embodiments.

"Natural or synthetic bone" is meant to refer to bone tissue, tissue resembling bone, synthetic material resembling bone, and tissue capable of forming bone. The term "bone" or "bone tissue" is intended for the purposes of the invention to refer to for example, an autograft bone, an allograft bone, or an xenograft bone. Such bone includes any bone from any source, including but not limited to bone from a living human donor, bone from a human cadaveric donor, and bone from an animal. The bone may include cortical bone and/or cancellous bone and/or cortico-cancellous bone. The term "bone fragment," as used in the present application refers to ground bone, pulverized bone, bone cubes, bone chips, bone strips, bone particles, and bone fibers. Bone fragments may be "bone particles" or "bone fibers," in some embodiments of the present invention. "Bone particle" refers to a piece of bone having an average diameter of between about 125 microns and about 4 mm. "Bone fiber" refers to a filament or thread of bone having an average thickness of between about 0.1 mm and about 2 mm and an average width of between about 0.3 mm and about 2.5 mm. Fibers can be of varying lengths. In certain embodiments, a bone fiber can have an average length of between about 1.0 mm and about 100 mm. In certain embodiments, bone fiber contains lamellae in the shape of threads or filaments having a median length to median thickness ratio of about 10:1. Synthetic material resembling bone comprises ceramics, hydroxyapatite, calcium phosphate, or calcium sulfate.

"Demineralized bone," as used in the present application refers to bone having less than about 8 wt % residual calcium. Demineralization involves treating the surface of a bone tissue to remove a surface layer of its inorganic mineral hydroxyapatite material leaving the mechanical properties of the organic phase of the bone constructs substantially unchanged. The level of demineralization of a bone tissue is defined by the amount (wt %) of residual calcium found in the demineralized bone. In some embodiments, the demineralized bone may contain physiologically active levels of growth and differentiation factors, for example, bone morphogenetic proteins (BMPs).

In some embodiments, the homogenized connective tissue may be prepared from allogenic or xenogenic tissue. Such connective tissue may be obtained from a human donor or an animal, such as bovine, porcine, or murine etc. Connective tissue may be obtained relatively economically. Varieties of connective tissue that may be used in certain embodiments of the present invention include but are not limited to areolar or loose connective tissue; adipose; dense, regular or irregular connective tissue; white fibrous; elastic connective tissue; and cartilage. Specific examples of connective tissues that may be used in certain embodiments of the present invention include, for example, fascia, dermis, tendons, ligaments, pericardium, urethra, small intestine, muscle, bone, and cartilage. Examples of different types of fascia that may be used in some embodiments of the present invention include: fascia lata, fascia adherens, fascia brachii, fascia axillaris, antebrachial fascia, abdominal fascia, internal fascia, fascia iliaca, fascia profunda, clavipectoral fascia, fascia cribosa, crucial fascia, deltoid fascia, dorsal deep fascia, pelvic fascia, fascia cruris, lumbar fascia, and pectoral fascia, among others. For practical reasons of availability during procurement and amount of fascia available, fascia lata from the anterior portion of the upper leg may be used in certain embodiments. Homogenized connective tissue may be prepared by methods involving, cleaning and disinfecting connective tissue, and removing extraneous tissues associated with the connective tissue. Connective tissues may be cut into small pieces to produce crudely fragmented connective tissue, and optionally triturated and washed with distilled/deionized endotoxin-free water and/or an aqueous solution, such as isotonic saline, among others. In processing, multiple "washes" may be affected using volumes of aqueous solution that are 10 times the approximated volume of the tissue being processed, in some embodiments. The use of three such processing steps may affect an approximate 1:1000 dilution of associated solubilizable elements rendering the tissue essentially free from such solubilizable elements. Connective tissue may be treated and homogenized at temperatures sufficient to produce a flowable homogenized connective tissue, in certain embodiments. The homogenized connective tissue may include connective tissue that has been reduced to particles that are uniformly small and evenly distributed. Homogenized connective tissue and/or the carrier may optionally include at least one of water, aqueous solutions, for instance isotonic saline, and water miscible polar organic solvents in addition to the connective tissue particles. The homogenized connective tissues used in methods of the present invention may include particles having an average diameter of less than about 50 microns, less than about 20 microns, or less than about 50 microns and greater than about 5 microns. In some embodiments, the homogenized connective tissue and optionally, at least one of a water miscible polar organic solvent, water and an aqueous solution, may be prepared by shear-induced shredding of connective tissue. A conventional blender may be used in preparing the homogenized connective tissue, in certain embodiments.

Certain methods for producing the inventive tissue repair implants may include preparing a connective tissue homogenate. Prior to homogenization, connective tissues, such as dermis, fascia, tendons, ligaments, pericardium, muscle, bone, urethra, small intestine, and cartilage, among others, may be crudely fragmented. Connective tissue, which may be fresh or freeze-dried, may be sliced, ground, carved, chipped, chopped, minced, cut, dissected, rent, ripped, sectioned, snipped, diced, shaved, comminuted, or trimmed into crude fragments. In some embodiments, the crude fragments may have an average diameter greater than about 50 microns. The crude fragments may be of varying sizes, in some embodiments. Essentially intact connective tissue or crude fragments of connective tissue, which may be fresh or freeze-dried, may be homogenized at least one time to prepare the homogenate. The homogenization step(s) of certain inventive methods may involve shear-induced shredding of connective tissue. Connective tissue may be homogenized to have tissue fragments having an average diameter of less than about 50 microns, less than about 20 microns, or less than about 50 microns and more than about 5 microns. Water, at least one aqueous solution, such as isotonic saline, or other components may be combined with a connective tissue before homogenization.

Certain methods include at least one of (a) heating a connective tissue before it is homogenized, (b) heating a connective tissue while it is being homogenized, and (c) heating a connective tissue homogenate. In some embodiments the heating is done to a temperature of between about ambient temperature and about 100° C., or between about 37° C. and about 100° C. The heating may be carried out for between about 0.5 minutes and about 30 minutes. The heating may be accomplished using sonication, microwave irradiation, or conventional heat transfer from a heating component, among other methods known in the art.

The tissue repair implant of the present invention has a "porous sponge-like structure". The term "porous sponge-like structure" refers to a three-dimensional structure that is porous, coherent, elastic, flexible, fibrous and resilient. In a dry state, the porous sponge-like implant of the present invention can quickly absorb fluid. In the wet state, the porous sponge-like implant of the present invention can maintain the porosity, cohesiveness, and integrity. The wet porous sponge-like structure can resist certain tensile stress, and bounce back and reabsorb fluid after being released from compression. The porous sponge-like implant can be twisted, folded, rolled, and inserted into the defect or wrapped around the defect of bone, cartilage or soft tissue.

General Description of the Process

In one embodiment, the present invention provides a process of making a tissue repair implant having a porous sponge-like structure. The process comprising preparing a connective tissue homogenate from one or more connective tissues; mixing the homogenate with a carrier solution to produce a connective tissue carrier; and mixing the connective tissue carrier with one or more natural or synthetic bone fragments to produce a tissue repair mixture. In another embodiment, the present invention provides a process of preparing a tissue repair implant having a porous sponge-like structure comprising obtaining a connective tissue homogenate from one or more connective tissues and mixing the connective tissue homogenate with a carrier solution, which does not contain natural or synthetic bone fragments, to produce a tissue repair mixture. A crudely fragmented connective tissue may be added into the tissue repair mixture to increase the integrity of the porous sponge-like structure. The connective tissue homogenate or the crudely fragmented connective tissue may be derived from one or more connective tissues of human or other animal(s). The natural or synthetic bone fragments may be in the form of particles, fibers, rods or cubes. The natural or synthetic bone fragments may have demineralized bone, partially demineralized bone, non-demineralized bone, ceramics, hydroxyapatite, calcium phosphate, calcium sulfate, calcium carbonate, or a combination of two or more of the above. In one embodiment of the invention, the mixture can be distributed in a pre-designed mold and kept at a temperature between 0° C. to about 30° C. to allow initial gelation and form a non-flowable mixture. In another embodiment of the invention, in order to maintain the porosity and an even distribution of pores within the porous sponge-like structure, the tissue repair mixture can be frozen first to solidify the structure and then optionally freeze-dried. A three-dimensional framework in the form of a web (FIG. 1), created by mixing the connective tissue homogenate with the carrier solution, may be treated with a treatment solution to further stabilize and increase the mechanical strength of the structure.

Certain embodiments of the present invention are directed to tissue repair implants comprising a plurality of demineralized bone fragments or non-demineralized bone fragment embedded in a porous three-dimensional framework. The framework may include at least one homogenized connective tissue and at least one carrier. In some embodiments, the tissue repair implant may be safely used in repairing damaged tissue, for instance bone in a patient. The tissue repair implant may, in some embodiments, be biocompatible, osteoinductive, and/or osteoconductive, such that it may ultimately be remodeled to a mineralized, hard tissue at the application site in vivo. In certain embodiments, the tissue repair implants may further include at least water, an aqueous solution, or a water miscible polar organic solvent. The tissue repair implant may include materials that improve handling or functional characteristics post-implantation. In some embodiments, the bone and connective tissue may be obtained from the same donor source (i.e., a single human cadaver donor). In certain embodiments, the tissue repair implant may be aseptic or sterile.

Each of the demineralized bone fragments and/or non-demineralized bone fragments and the homogenized connective tissue of the inventive implant may include materials derived from allogenic or xenogenic sources. In certain embodiments, bone and connective tissues obtained from vertebrate species, for example human, bovine, porcine, ovine, caprine, and piscene sources may be used to prepare demineralized bone fragments and carrier. The plurality of bone fragments may include more than one type of bone tissue (e.g., cancellous, cortical, or cortico-cancellous bone), and the homogenized connective tissue may include more than one type of connective tissue (i.e., fascia and tendon). The plurality of demineralized bone fragments and/or non-demineralized bone fragments may include bone from a single donor source, or from multiple donor sources, and the homogenized connective tissue may also include tissue from a single donor source, or from multiple donor sources.

Composition

In one embodiment, the water insoluble porous sponge-like implant of the present invention comprises an uniform composition containing evenly distributed connective tissue homogenate and carrier that forms a three-dimensional framework. In another embodiment, the implant of the present invention comprises a uniform composition containing a connective tissue homogenate and carrier framework interspersed with bone fragments. The connective tissue homogenate and the carrier form a uniform framework which traps or embraces the bone fragments.

Connective Tissue Homogenate

The connective tissue homogenate may have excellent histocompatibility and elicit minimal antibody formation or immunological rejection, in certain embodiments. The homogenized connective tissue may be made acellular by treating it with detergents, endonucleases and decontaminating agents.

A devitalized process used to prepare homogenized connective tissue of the present invention may be performed without damage to matrix and/or tissue structure, in some embodiments and may employ detergents, sarcosinates, and decontaminating agents. The matrix structure may include collagens, hyaluronins, elastins, mucopolysaccharides and proteoglycans, among other components. Connective tissue that is devitalized may have a thickness that does not exceed about 8 mm, about 6 mm, or about 4 mm, in certain embodiments. Devitalization processing may be altered to accommodate the thicker tissues.

In certain aspects, the tissue repair implant may include no more than about 80 wt %, no more than about 50 wt %, or no more than about 20 wt % of the connective tissue homogenate in the dry state. The amount of connective tissue homogenate added in a tissue repair implant may be varied to adjust the viscosity and gelation characteristics of the tissue repair mixture as well as the re-hydration characteristics of the porous sponge-like structure. Moreover, incorporating connective tissue homogenate in the tissue repair mixture, specifically, in the connective tissue carrier, may strengthen the three-dimensional framework and increase the integrity of the porous sponge-like structure. Incorporating connective tissue homogenate in the tissue repair mixture also may increase the cellular response towards the framework of the porous sponge-like structure by facilitating cellular attachment, migration, and proliferation since the connective tissue homogenate comprises natural or heat-denatured collagen.

Crudely Fragmented Connective Tissue

In certain embodiments, the tissue repair implant may include between about 0.25 wt % and about 95 wt %, or between about 0.5 wt % and about 90 wt % of the crudely fragmented connective tissue in the dry state. The amount of crudely fragmented connective tissue added in a tissue repair mixture may be varied to adjust the gelation characteristics and prevent shrinkage of the tissue repair mixture during initial gelation, freeze-drying, and/or one or more treating steps with treatment solution. The crudely fragmented connective tissue may also provide structure reinforcement and further increase the integrity and mechanical strength of the porous sponge-like structure. Moreover, incorporating crudely fragmented connective tissue in the tissue repair implant may further increase the cellular response by facilitating cellular attachment, proliferation, and migration since the crudely fragmented connective tissue comprises collagen.

DBM/Bone

In certain embodiments, the tissue repair implant may include demineralized bone fragments having less than about 8 wt % or less than about 4 wt % residual calcium. The tissue repair implant may include demineralized bone fragments having between about 0.5 wt % and about 4 wt % residual calcium, about 1 wt % and about 4 wt %, or about 2 wt % and about 4 wt % in certain embodiments.

The plurality of demineralized bone fragments may include at least one of demineralized bone particles and demineralized bone fibers, in some embodiments. The demineralized bone fragments may include materials derived from allogenic or xenogenic sources. The demineralized bone fragments may be derived from cortical bone or cancellous bone. In certain embodiments, the plurality of demineralized bone fragments may include at least one of demineralized allogenic cortical bone particles, demineralized xenogenic cortical bone particles, demineralized allogenic cancellous bone particles, or demineralized xenogenic cancellous bone particles.

Certain tissue repair implants of the present invention may include demineralized bone particles. Demineralized bone particles may be prepared from cleaned and disinfected bone fragments that have been freeze-dried and ground/fractured into bone particles. Bone particles may be selected by, for example, using sieving devices (i.e., mesh sieves) commercially available for obtaining particles within a desired size range. Such demineralized bone particles may have an average diameter of between about 125 microns and about 4 mm; between about 710 microns and about 2 mm; between about 125 microns and about 500 microns; between about 125 microns and about 850 microns; between about 125 microns and about 710 microns; or between about 250 microns and about 710 microns. Certain embodiments of the present invention may include demineralized bone particle that is commercially available. For example, a suitable demineralized bone particle that is widely and reliably available is produced by LifeNet Health, Virginia Beach, Va.

Some tissue repair implants of the present invention may include demineralized bone fibers. In certain embodiments, the demineralized bone fibers may have an average thickness of between about 0.1 mm and about 0.3 mm and an average width of between about 0.3 mm and about 1.0 mm. The length of the fibers may vary. In some embodiments, the demineralization process begins by producing bone particles having an average diameter size range of between about 1 mm and about 2 mm or bone fibers having an average dimension of 0.1 mm to 0.3 mm thickness and an average width of about 0.3 mm to about 1 mm. The fragments may then be treated with cleaning solutions. If the bone to be processed into fragments has not been previously cleaned and/or disinfected, they may be cleaned and or disinfected by the use of detergents, hydrogen peroxides, antibiotics, and/or alcohols to affect a removal of associated tissues such as bone marrow and cellular elements. Following cleaning and disinfection, these fragments (i.e., particles and fibers) may be demineralized by exposure to dilute hydrochloric acid to affect a removal/reduction of the mineral component of the bone fragments (i.e., particles and fibers). Such additional processing may, in some instances, inactivate potential viral contamination (i.e., HIV and hepatitis viruses, among others).

Certain embodiments of the present invention are directed to methods for the preparation of inventive tissue repair implant having a porous sponge-like structure, as described above. Such methods include combining a homogenized connective tissue, a carrier solution, a plurality of demineralized or non-demineralized bone fragments, and crudely fragmented connective tissue. The tissue repair implant having a porous sponge-like structure can contain between about 0.1 wt % and about 95 wt % or between about 10 wt % and about 90 wt % demineralized or non-demineralized bone fragments. Bone fragments may include at least one of bone particles and bone fibers from bone tissue. Some methods of preparing the tissue repair implants of the present invention may include the production of particles or fibers from bone tissue, as discussed above. Bone fragments may be demineralized, as described above, in certain embodiments. The fragments may be demineralized to have less than about 8 wt % residual calcium, less than about 4 wt % residual calcium, between about 0.5 wt % and about 4 wt % residual calcium, between about 1 wt % and about 4 wt % residual calcium, or between about 2 wt % and about 4 wt % residual calcium, in some methods of the present invention. Certain methods of the present invention may include freeze-drying demineralized bone fragments. In some embodiments, the demineralized bone fragments may be freeze-dried to a point such that the freeze-dried fragments have an average residual moisture of less than about 10 wt %, or less than about 5 wt %. In some embodiments, freeze-dried demineralized bone fragments may be rehydrated before use in preparing the tissue repair implants having a porous sponge-like structure of the present invention. Rehydrated freeze-dried demineralized bone particles may have a residual moisture content of less than about 80 wt %, less than about 50 wt %, less than about 25 wt %, or between about 10 wt % to about 25 wt %, in certain embodiments.

Carrier Solution

In some embodiments of the present invention, the connective tissue carrier will contain a carrier solution in addition to the connective tissue homogenate. Due to the hydrophilic nature of the connective tissue homogenate and the carrier solution, these two components can penetrate each other and fully integrate so that the connective tissue carrier can form a three-dimensional framework to entrap the natural or synthetic bone fragments. The carrier solution can function as a diluent for the connective tissue homogenate to increase the porosity in the final porous sponge-like structure as well as to change the thickness of the web wall of the three-dimensional framework after one or more freeze-dry cycles. Addition of the carrier solution may change the viscosity of the tissue repair mixture so that the natural or synthetic bone fragments, such as demineralized or non-demineralized bone fragments, will remain "afloat" and evenly distributed in the wet state of tissue repair mixture. The weight percentage of the carrier in the tissue repair implant is no more than 20% and more preferably no more than 5% in the dry state.

The carrier solution may comprise alginate, propylene glycol alginate, native or crosslinked chitosan, starch, polyethylene glycol, cellulose and its derivatives (such as cellulose acetate, carboxymethyl cellulose, and methyl cellulose), xanthan gum, dextran, hyaluronic acid, chondroitin sulfate, locust bean gum, gum tragacanth, gum arabic, curdlan, pullulan, scleroglucan, lower methoxylpectin, or carrageenan. The carrier solution may comprise salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The carrier solution may also comprise natural and or synthetic polymers selected from the group comprising native or modified collagen, gelatin, agarose, modified hyaluronic acid, fibrin, chitin, biotin, avidin, MATRIGEL®, HUMAN EXTRACELLULAR MATRIX®, proteoglycans, laminin, fibronectin, elastin, heparin, glycerol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, polylactic acid, or a combination comprising at least one of the foregoing polymers.

In one embodiment of the present invention, a water replacing agent, such as glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, or lipids, can be included in the carrier solution to increase the flexibility of the porous sponge-like structure in the dry state and act as a moisture barrier. In another embodiment of the present invention, the carrier solution can also include one or more agents that have bioactive supplement binding site(s) so that when the porous sponge-like structure is implanted in vivo or exposed to a biological environment, it can attract cells or bioactive agents from the environment to the porous sponge-like structure to facilitate the healing process. Agents that have one or more bioactive supplement binding sites include but are not limited to hyaluronan, heparin, heparin sulfate, keratin sulfate, dermatan sulfate, chondroitin sulfate, betaglycan, heparan sulfate proteoglycan, syndecan, biglycan, or decorin.

In one embodiment of the present invention, the carrier solution may also include one or more bioactive supplements to directly stimulate the healing process. The bioactive supplements may be growth factors, differentiation factors, cytokines, or anti-inflammatory agents. The growth or differentiation factors may be for example, a growth factor of the FGF-family or TGF-family, IGF-1, PDGF, EGF, VEGF, HGF, PTHrP, Ihh, dexamethasone, insulin, transferrin, selenium, ITS, ascorbate, or a combination thereof. The cytokines may include GM-CSF, G-CSF, TNF-$\alpha$, IL-1$\beta$, IL-4, IL-6, IL-8, IL-10, SLP1, MCP1, MIP-1$\alpha$, MIP-2, IL-18, angiopoietin, KGF, endothelin, IFN-$\alpha$, or IFN-$\beta$. Examples of anti-inflammatory agents may include an IL-1$\alpha$R antibody, TNF-$\alpha$ receptor antagonist, cyclooxygenase-2 specific inhibitors, MAP kinase inhibitors, NO synthase inhibitors, NF-$\kappa$B inhibitors, or inhibitors of MMP. The carrier solution may include bioactive supplements extracted from tissue comprising demineralized bone matrix, basement membrane, or submucosa matrix. The carrier solution may also include antioxidants, for instance, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene to protect bioactive components from oxygen-radical-induced damage antioxidants.

Processing

In certain methods, the tissue repair implant may be cast in a mold. In some embodiments, a method may further include freeze-drying a cast composition or crosslinking a cast composition using ionic, enzymatic, chemical; or photoactive agents known in the art. In one preferred embodiment, a cast tissue repair implant can be freeze-dried first to obtain the porosity, allow even distribution of pores within the porous sponge-like structure, and at the same time to entrap natural or synthetic bone fragments within the three-dimensional framework created by the connective tissue carrier. In order to stabilize the framework of the porous sponge-like structure, further entrap the natural or synthetic bone fragments, and increase the mechanical strength of the structure, the freeze-dried porous sponge-like structure can be treated with a treatment solution. The treatment solution may comprise ionic, enzymatic, chemical, or photoactive crosslinking agents. Examples of ionic crosslinking agents include but are not limited to metal ions selected from the group consisting of calcium, barium, aluminum, strontium, copper, zinc, magnesium, manganese, cobalt, and iron. Other ionic crosslinking agents include compounds containing phosphate-bearing groups, or compounds that are sulfates or citrates. Examples of enzymatic crosslinking agents include but are not limited to transglutaminase, ethylenediamine, lysyl oxidase family, hexamethylene diisocyanate (HMDIC), dimethyl suberimidate (DMS), or dimethyl-3-3'-dithiobispropionimidate (DTBP). Examples of chemical crosslinking agents include but are not limited to glutaraldehyde, glyceraldehyde, genipin, glucose or ribose, poly(ethylene glycol) diepoxide crosslinker, poly(ethylene glycol) diglycidyl ether, EDC and NHS, or acryl azide.

Accordingly, the treatment solution may comprise agents such as but not limited to salts of calcium, barium, aluminum, strontium, copper, zinc, magnesium, manganese, cobalt, or iron; glutaraldehyde, glyceraldehyde, genipin, glucose or ribose, poly(ethylene glycol) diepoxide crosslinker, poly(ethylene glycol) diglycidyl ether, EDC and NHS, transglutaminase, ethylenediamine, lysyl oxidase family, hexamethylene diisocyanate (HMDIC); dimethyl suberimidate (DMS), dimethyl-3-3'-dithiobispropionimidate (DTBP), or acryl azide. The treatment solution may also comprise natural and or synthetic polymers selected from the group comprising native or modified collagen, gelatin, agarose, modified hyaluronic acid, fibrin, chitin, biotin, avidin, demineralized bone matrix, MATRIGEL®, HUMAN EXTRACELLULAR MATRIX®, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, or polylactic acid, or a combination comprising at least one of the foregoing polymers. The treatment solution may also include bioactive supplements. The bioactive supplements may be growth factors, differentiation factors, cytokines, or anti-inflammatory agents. Examples of growth or differentiation factors may include the FGF-family, TGF-family, IGF-1, PDGF, EGF, VEGF, HGF, PTHrP, Ihh, dexamethasone, insulin, transferrin, selenium, ITS, ascorbate, or a combination thereof. Cytokines may include, for example, GM-CSF, G-CSF, TNF-$\alpha$, IL-1$\beta$, IL-4, IL-6, IL-8, IL-10, SLP1, MCP1, MIP-1$\alpha$, MIP-2, IL-18, angiopoietin, KGF, endothelin, IFN-$\alpha$, or IFN-$\beta$. The anti-inflammatory agents may include but are not limited to an IL-1$\alpha$R antibody, TNF-$\alpha$ receptor antagonist, cyclooxygenase-2 specific inhibitors, MAP kinase inhibitors, NO synthase inhibitors, NF-$\kappa$B inhibitors, or inhibitors of MMP. The treatment solution may also include agents having bioactive supplement binding site(s) comprising hyaluronan, heparin, heparin sulfate, keratin sulfate, dermatan sulfate, chondroitin sulfate, betaglycan, heparan sulfate proteoglycan, syndecan, biglycan, or decorin.

Since the porous sponge-like structure in the tissue repair implant has been created by freeze-drying before the application of one or more treating steps, the treatment solution can easily penetrate and evenly distribute into the entire porous sponge-like structure, which can significantly shorten the duration of treatment to about one or two hours. Shortening the treatment is vitally important for maintaining the biological function of the bioactive component present in the bone particles, such as BMPs in the demineralized bone matrix, which are prone to be inactivated by hydration. After treating with the treatment solution, the stabilized porous sponge-like structure may be washed with isotonic, hypertonic, or hypotonic solution. Then the porous sponge-like structure can be freeze-dried again and stored dry. In one embodiment of the present invention, a water replacing agent such as glycerol (glycerin USP), adonitol, sorbitol, ribitol, galactitol, D-galactose, 1,3-dihydroxypropanol, ethylene glycol, triethylene glycol, propylene glycol, glucose, sucrose, mannitol, xylitol, meso-erythritol, adipic acid, proline, hydroxyproline, polyethylene glycol, alcohol, or lipids may be applied to increase the flexibility of the porous sponge-like structure in the dry state and act as a moisture barrier. The porous sponge-like structure may be treated with a water replacing agent and then stored wet. The porous sponge-like structure can also be treated with a water replacing agent and then freeze-dried and stored.

In one embodiment of the present invention, the functionally active tissue repair implant can be combined with one or more bioactive supplements. Examples of bioactive supplements include growth factors, differentiation factors, cytokines, and anti-inflammatory agents. In another embodiment of the present invention, the tissue repair implant can be combined with one or more agents that have bioactive supplement binding sites through covalent coupling or adsorption to increase the affinity of a bioactive supplement to the tissue repair implant. Agents that have bioactive supplement binding sites may be one or a combination of extracellular matrix proteins. Agents that have one or more bioactive supplement binding sites may be a natural or synthetic molecule comprising hyaluronan, heparin, heparin sulfate, keratin sulfate, dermatan sulfate, chondroitin sulfate, betaglycan, heparan sulfate proteoglycan, syndecan, biglycan, or decorin. Moreover, an extra functional segment that is from a group, but not limited to, COOH, NH2, or OH can be added to the natural or synthetic proteins or peptides to facilitate the coating. The extra functional segment can be from groups that change the hydrophilicity or charge. In one embodiment, one or more bioactive supplements or one or more agent(s) that have bioactive supplement binding sites can be incorporated in one or more treatment solutions. In another embodiment, coating with one or more bioactive supplements or one or more agent (s) that have bioactive supplement binding sites can be conducted after one or more treating steps with the treatment solution. Yet, in another embodiment, coating with one or more bioactive supplements or one or more agent(s) that have bioactive supplement binding sites can be conducted during or right before clinical application.

In one embodiment, one or more polysaccharides are included in the carrier solution in the tissue repair mixture. The preferred polysaccharide comprises alginate, propylene glycol alginate, native or crosslinked chitosan, starch, cellulose and its derivatives (such as cellulose acetate, carboxymethyl cellulose, and methyl cellulose), xanthan gum, dextran, locust bean gum, gum tragacanth, gum arabic, curdlan, pullulan, scleroglucan, lower methoxylpectin, or carrageenan. Due to the hydrophilic nature of the connective tissue homogenate and the polysaccharide solution, these two components can penetrate each other and fully integrate so that the connective tissue carrier can form a three-dimensional framework to entrap solid components such as the natural or synthetic bone fragments. In addition, due to the ionic nature of the polysaccharides, by adjusting the pH of the mixture, it is possible to control the ionic interaction between the carrier solution and the collagen components in the crudely fragmented connective tissue as well as in the connective tissue homogenate so that an enhancement of the gelation occurs in the tissue repair mixture and a non-flowable mixture can be obtained before freezing or freeze-drying. In one embodiment of the present invention, the tissue repair mixture can be freeze-dried first to produce a three-dimensional framework created by the mixture of connective tissue homogenate and the polysaccharide solution, allow even distribution of pores within the porous sponge-like structure, and at the same time to entrap natural or synthetic bone fragments within the framework. The dried polysaccharide(s) present in the porous sponge-like structure may be further treated with covalent and/or ionic-crosslinking agents. An ionic-crosslinking agent may be employed because it is easy to apply and is not likely to cause modification of the bioactive components in the bone particles, such as BMPs in the demineralized bone matrix. In one embodiment, sodium alginate with viscosity from about 20 to about 200 and G/M ratio larger than 1 may be mixed with the connective tissue homogenate and freeze-dried to produce a stable three-dimensional framework of the porous sponge-like structure. The porous sponge like structure may then be treated with a solution of divalent salt such as calcium salt and/or a positively charged solution such as poly-L-lysine or chitosan. The treatment step may be conducted for a period of time of about 5 minutes to about 16 hours, from 15 minutes to about 120 minutes, or between 30 minutes to 60 minutes. Treatment of calcium salt on freeze dried porous sponge-like structure instead of the gel-like tissue repair mixture before freeze drying has multiple advantages. For example, treatment of calcium salt on freeze dried porous sponge-like structure does not limit the diffusion of the calcium salt throughout the entire porous sponge-like structure and may produce (a) a stronger and evenly distributed cross-links within the porous sponge-like structure; (b) a porous sponge-like structure that can absorb more fluid in less time; and (c) a larger pore area that can accommodate more natural or synthetic bone fragments within a three-dimensional framework of web. Moreover, treatment of calcium salt on freeze-dried porous sponge-like structure will not crosslink the surface first and form a highly crosslinked surface and an unreacted core (inhomogeneous), which will likely occur if treatment of calcium salt is conducted before freeze-drying. The crosslinked surface can decrease and even inhibit the diffusion of the calcium salt towards the core of the structure. In another embodiment of the present invention, application of the calcium salt not only may crosslink the polysaccharide such as sodium alginate, but also may become a source of mineralization in subsequently induced new bone formation. Moreover, comparing to the framework formed by alginate only, versus one that incorporates the connective tissue homogenate in the alginate solution, the latter can increase the strength and integrity of the three-dimensional framework and produce a porous sponge-like structure that is stronger, more resilient, and can better entrap bone fragments. The weight percentage of the polysaccharide incorporated in the final dry state of the porous sponge-like structure is less than about 20%, less than about 10%, or less than about 5%.

Three-dimensional (3-D) macro-porous sponge-like structure in the present invention is designed to provide support for the cells until they are organized into a functioning tissue. After implantation, the architecture of the macro-porous sponge-like structure can control the extent of vascularization and tissue ingrowth. The pores of the porous sponge-like structure in the present invention will be highly interconnected, between about 10 to about 800 μm, preferably between about 50 to about 300 μm. The pores can occupy about 10 to about 95% of the volume in a dry state. The pore size and volume can be adjusted by adding porogens, application of inert gas, or application of a negative hydrostatic pressure before freeze-drying the tissue repair mixture.

Sterilization

Methods of the current invention may include sterilization of the functional tissue repair implants having a porous sponge-like structure, components of tissue repair implants, and/or sterilization of packaged tissue repair implants having a porous sponge-like structure. Sterilization may involve the use of ionizing radiation, in some embodiments. In other embodiments, the absorbed dose of ionizing radiation may be between about 8.0 KGy and about 50 KGy, between about 8.0 KGy and about 25 KGy, or between about 8.0 KGy and about 18 KGy. In some embodiments, the sterilizing step may include placing the packaged tissue repair implants having a porous sponge-like structure on dry ice and irradiating the packaged composition. In certain embodiments, sterilization may be performed at a temperature of between about −20° C. and −50° C.

Certain tissue repair implants of the present invention may include other elements. Additional elements may include but are not limited to antibiotics (i.e., penicillin), antiviral agents (i.e., Triton X-100, Nonidet P-40, N-lauroyl sarcosinate, Brij-35, and peroxide generating agents), antitumor agents, analgesics, immunosuppressive agents (i.e., bovine intestinal alkaline phosphatase), permeation enhancers (i.e., fatty acid esters, such as the laurate, myristate and stearate monoesters of polyethylene glycol), or nucleic acids.

Implantation

The present invention also provides a method of repairing a damaged tissue such as but not limited to a bone, cartilage, or soft tissue. The method comprises implanting the tissue repair implant at the site of the damaged tissue to promote repair or regeneration of the tissue. The present invention also provides a method of inducing tissue formation comprising providing the tissue repair implant to the site of defect to induce tissue formation or regeneration.

In some embodiments, for on-site preparation, the tissue repair implant having a porous sponge-like structure can be applied directly without re-hydration to allow the tissue repair implant to absorb blood or fluid as well as autologous cells in situ. On-site preparation has the advantage that permits the addition of optional components at the discretion of the clinician. Prior to implantation, the freeze-dried tissue repair implant can be re-hydrated with one or a cocktail of bioactive supplements or autologous or allogenic bone marrow aspirate, blood, or platelet rich plasma. Alternatively, the tissue repair implant can be combined with one or more bioactive supplements or one or more agent(s) that has bioactive supplement binding sites through covalent coupling or adsorption prior to the clinical application to increase the affinity of exogenous or endogenous bioactive supplement or cytokine to the porous sponge-like structure.

In some embodiments, the tissue repair implant may be seeded with vital cells to render the tissue repair implant vital just prior to implantation. Alternatively, the tissue repair implant can be seeded with vital cells and cultured in vitro for certain duration and then implanted. The vital cells may comprise one or ore than one type of cells from autologous or allograft bone marrow aspirate; stromal cells from bone marrow, stromal cells from fat, synovium, periostieum, perichondrium, muscle, dermis, umbilical cord blood, and Warton's jelly; or pericytes.

In some embodiments, the tissue repair implant may be provided in a wet state where a water replacing agent can be present. The tissue repair implant may be sufficiently flexible to allow easy insertion into or wrapping around the defect. The present of water replacing agent will also allow fast fluid exchange and absorption of the fluid such as blood into the tissue repair implant.

In some embodiments, the tissue repair implant may be provide in a unitary kit that also include a re-hydration agent, a bioactive agent, a bioactive cocktails, or one or more agents that has bioactive supplement binding sites.

Without further description, it is believed that one of ordinary skill in the art can, using the preceding description and the following illustrative examples, make and utilize the claimed invention. The following working examples therefore, specifically point out preferred embodiments of the present invention, and are not to be construed as limiting in any way the remainder of the disclosure.

EXAMPLES

Example 1

Preparation of Tissue Repair Implants: Porous Sponge-Like Structure with DMB Particles Fascia lata and bone from a human cadaver were procured and returned to the processing facility under sterile conditions. Donor histories, personal and medical, were obtained following accepted standards of the American Association of Tissue Banks. Microbiological tests were performed following FDA guidelines for testing sterility of products.

The bone and fascia were cleaned of unwanted tissues and freeze-dried. The freeze-dried fascia was cut into small (about 1.5 cm by 1.5 cm) pieces (e.g., crude fragments). Sterile water in a volume (1 cm$^3$ of isotonic saline corresponds to about 1 g) approximating 20 times the weight of tissue, was added to a container containing the cut fascia. The ingredients were heated to a temperature of 100 degree C. using a hot plate, and maintained at this temperature for about 5 minutes. Optionally, water was added to the heated composition to replace the liquid lost to evaporation. The heated composition was transferred into a conventional blender and mechanically homogenized (e.g., blended) for about 1 to 3 minutes. The homogenized connective tissue was re-heated for an additional 3 minutes on a hot plate, and mechanical homogenization was repeated for an additional 4 minutes (e.g., until the mixture was liquefied and homogeneous).

Ground demineralized bone powder was prepared by impact fragmentation of bone, followed by freeze-drying. The freeze-dried particles were sized using mesh sieves. Ground demineralized bone particles having a size in the range of about 250 to 710 microns and demineralized to an average weight percent residual calcium of 2±1% were used.

Crudely fragmented fascia was made by blending them in a small blender until the fascia fiber diameter is less than 2 mm. Alginate solution was prepared by dissolving alginate powder (Protanal, LF 10/60, FMC Biopolymer, Dramen, Norway) in sterile water to a final concentration of 0.5 to 2%. The solution was filter sterilized and stored at 2° C.-1° C. until use. CaCl$_2$ solution was made by dissolving CaCl$_2$ powder (FW=147.02, Mallinckrodt, Hazelwood, Mo.) in sterile water to a final concentration of 100 mM. The solution was filter sterilized and stored at ambient temperature (16° C.-30° C.) until use.

To prepare the tissue repair implant, the homogenized fascia was mixed with a sodium alginate solution first to produce a connective tissue carrier that was mixed further with crudely fragmented fascia and sized, freeze-dried demineralized bone powder. After mixing all the components, the mixture was distributed into molds with pre-determined shapes and sizes, freeze-dried for 48 to 72 hours, treated with CaCl$_2$ for 0.25, 0.5, 1, or 2 hours, washed with water, and freeze-dried again for 48 to 96 hours. Before the first freeze-drying cycle, some samples were exposed to a negative hydrostatic pressure to allow the expansion of the DBM mixture to a preset thickness. The resultant porous DBM structure was then sent out for sterilization by gamma irradiation.

In one of the tissue repair implants, the porous DBM structure contained about 91% DBM particle, 3% alginate, 5% homogenized fascia, and 1% fascia fiber by dry weight. In another tissue repair implant, the porous DBM structure contained about 70% DBM particle, 3% alginate, 12% homogenized fascia, and 15% fascia fiber by dry weight. The freeze-dried, molded, tissue repair implants demonstrated high mechanical strength and maintained the shape of their mold.

Example 2

Preparation of Tissue Repair Implants: Porous Sponge-Like Structure without Bone Fragment The homogenized fascia, sodium alginate solution, crudely fragmented fascia, and $CaCl_2$ solution were prepared as described in Example 1.

To prepare the tissue repair implant, the homogenized fascia was mixed with a sodium alginate solution first to produce a connective tissue carrier, which was mixed further with crudely fragmented fascia. After mixing all the components, the mixture was distributed into molds with pre-determined shapes and sizes, freeze-dried, treated with $CaCl_2$, washed, and freeze-dried again. Before the first freeze-drying cycle, some samples were exposed to a negative hydrostatic pressure to allow the expansion of the mixture to a preset thickness. The resultant porous sponge-like structure was then sent out for sterilization by gamma irradiation.

In one of the tissue repair implants, the porous sponge-like structure contained about 20% alginate, 60% homogenized fascia, and 20% fascia fiber by dry weight. The freeze-dried, molded, tissue repair implants demonstrated high mechanical strength and maintained the shape of their mold.

Example 3

Preparation of Tissue Repair Implants: Porous Sponge-Like Structure with DBM Particles and DMB Fiber Bone The homogenized fascia, sodium alginate solution, crudely fragmented fascia, demineralized bone powder, and $CaCl_2$ solution were prepared as described in Example 1.

Demineralized fiber bone was prepared by cutting cortical bone to produce cut fiber bone having an average length from about 1 mm to about 100 mm. Then the cut fiber bone was cleaned and disinfected, and a total of 463 grams of bone materials were demineralized to 2.5% residual calcium using 2 cycles of 0.5 N HCl and acid volumes of 4.0 liters/cycle and 3.0 liters/cycle, 1 cycle of ultrapure water of 3.0 liters/cycle, and 2 cycles ultrapure water plus buffer of 3.0 liters/cycle to terminate the demineralization process. The bone fibers were finally washed in 3.0 liters of ultrapure water, stored frozen at −80 degree C. in a sterile container, and freeze-dried for 96 hrs.

To prepare the tissue repair implant, the homogenized fascia was mixed with a sodium alginate solution first to produce a connective tissue carrier, which was mixed further with demineralized fiber bone and sized, freeze-dried demineralized bone powder. After mixing all the components, the mixture was distributed into molds with pre-determined shapes and sizes, freeze-dried, treated with $CaCl_2$, washed with water, and freeze-dried again. The resultant porous sponge-like structure was then sent out for sterilization by gamma irradiation. Before the first freeze dry cycle, some samples were exposed to a negative hydrostatic pressure to allow the expansion of the mixture to a preset thickness. In one of the tissue repair implants, the porous sponge-like structure contains about 70% DBM particle, 17% demineralized fiber bone, 3% alginate, and 10% homogenized fascia by dry weight. In another tissue repair implant, the porous sponge-like structure contains about 56% DBM particle, 35% demineralized fiber bone, 2.5% alginate, and 6.5% homogenized fascia by dry weight. The freeze-dried, molded, tissue repair implants demonstrated high mechanical strength and maintained the shape of their mold.

Example 4

Preparation of Tissue Repair Implants: Porous Sponge-Like Structure with DBM Fiber Bone The homogenized fascia, sodium alginate solution, demineralized fiber bone, and $CaCl_2$ solution were prepared as described in Example 1 and Example 3.

To prepare a tissue repair implant, the homogenized fascia was mixed with a sodium alginate solution first to produce a connective tissue carrier, which was mixed further with demineralized fiber bone. After mixing all the components, the mixture was distributed into molds with pre-determined shapes and sizes, freeze-dried, treated with $CaCl_2$, washed with water, and freeze-dried again. The resultant porous sponge-like structure was then sent out for sterilization by gamma irradiation.

In one of the tissue repair implants, the porous sponge-like structure contained about 87% demineralized fiber bone, 3% alginate, and 10% homogenized fascia by dry weight. The freeze-dried, molded, tissue repair implants demonstrated high mechanical strength and maintained the shape of their mold.

Example 5

Preparation of Tissue Repair Implants: Flexible Porous Sponge-Like Structure with DBM Particles The homogenized fascia, sodium alginate solution, demineralized bone powder, and $CaCl_2$ solution were prepared as described in Example 1.

To prepare the tissue repair implant, the homogenized fascia was mixed with a sodium alginate solution first to produce a connective tissue carrier, which was mixed further with sized, freeze-dried demineralized bone powder. After mixing all the components, the mixture was freeze-dried, treated with $CaCl_2$, washed with water. Then the porous sponge-like structure was soaked in about 99.5% glycerol solution for about 1 hr. The excessive glycerol solution was removed and the porous sponge-like structure was freeze-dried again. The resultant flexible porous sponge-like structure was then sent out for sterilization by gamma irradiation.

In one of the tissue repair implants, the porous sponge-like structure contained about 26% DBM particle, 1% alginate, 3% homogenized fascia, and 70% of glycerol by dry weight. The freeze-dried, molded, tissue repair implants demonstrated high mechanical strength and maintained the shape of their mold.

Example 6

Preparation of Tissue Repair Implants: Porous Sponge-Like Structure with DBM Particles and High or Low Dose of Heparin The homogenized fascia, sodium alginate solution, crudely fragmented fascia, demineralized bone powder, and $CaCl_2$ solution were prepared as described in Example 1. Heparin stock solution was prepared by dissolving heparin sodium salt grade I-A from porcine intestinal mucosa (Sigma, St. Louis, Mo.) in sterile water to a final concentration of 10 mg/mL. The solution was filter sterilized and stored at 2° C.-10° C. until use.

To prepare the tissue repair implant, the homogenized fascia was mixed with a sodium alginate solution, and various amount of heparin solution to produce a connective tissue carrier, which was mixed further with crudely fragmented fascia and the sized, freeze-dried demineralized bone powder. After mixing all the components, the mixture was distributed into molds with pre-determined shapes and sizes, freeze-dried, treated with $CaCl_2$, washed with water, and freeze-dried again for. The resultant porous sponge-like structure was then sent out for sterilization by gamma irradiation.

In one of the tissue repair implants, the porous sponge-like structure contained about 70% DBM particle, 2.9% alginate, 12% homogenized fascia, and 15% fascia fiber, and 0.1% heparin by dry weight. In another tissue repair implants, the porous sponge-like structure contained about 70% DBM particle, 2.6% alginate, 12% homogenized fascia, and 15% fascia fiber, and 0.4% heparin by dry weight. The freeze-dried, molded, tissue repair implants demonstrated high mechanical strength and maintained the shape of their mold.

Example 7

Preparation of Tissue Repair Implants: Porous Sponge-Like Structure with Ground Cortical Bone Particles The homogenized fascia, sodium alginate solution, crudely fragmented fascia, and $CaCl_2$ solution were prepared as described in Example 1.

Ground cortical (GC) bone powder was prepared by impact fragmentation of bone, followed by freeze-drying. The freeze-dried particles were sized using mesh sieves. Ground cortical bone particles having a size in the range of about 250 to 1000 microns were used.

To prepare the tissue repair implant, the homogenized fascia was mixed with a sodium alginate solution to produce a connective tissue carrier, which was mixed further with crudely fragmented fascia, and the sized, freeze-dried ground cortical bone powder. After mixing all the components, the mixture was freeze-dried, treated with $CaCl_2$, washed with water, and freeze-dried again. The porous sponge-like structure was then sent out for sterilization by gamma irradiation.

In one of the tissue repair implants, the porous sponge-like structure contained about 85% GC particles, 3% alginate, 6% homogenized fascia, and 6% fascia fiber by dry weight. The freeze-dried, molded, tissue repair implants demonstrated high mechanical strength and maintained the shape of their mold.

Example 8

Preparation of Tissue Repair Implants: Porous Sponge-Like Structure with GC Particles Crosslinked with Genipin The homogenized fascia, sodium alginate solution, crudely fragmented fascia, and ground cortical bone powder were prepared as described in Example 1 and Example 7. Genipin stock solution was made by dissolving genipin (MW=226.2, Sigma) in 40% molecular grade ethanol to a final concentration of 100 mg/ml. The solution was filter sterilized and used right away.

To prepare the tissue repair implant, the homogenized fascia was mixed with various amounts of genipin solution to produce a connective tissue carrier. The wet weight percentage of genipin was 1%, 0.5%, or 0.25% in the tissue repair mixture. Then the connective tissue carrier was mixed further with crudely fragmented fascia and the sized, freeze-dried ground cortical bone powder. After mixing all the components, the mixture was distributed into molds with pre-determined shapes and sizes and kept in dark for 4 to 16 hours at room temperature to allow crosslinking by genipin to occur. The structure turned dark blue after crosslinking. Then the crosslinked and molded structure was washed to remove unbound genipin and freeze-dried. The resultant porous sponge-like structure was then sent out for sterilization by gamma irradiation. The freeze-dried, molded, tissue repair implants with 1% genipin in the wet mixture demonstrated higher mechanical strength than the ones with 0.5 or 0.25% genipin in the wet mixture.

Example 9

Preparation of Tissue Repair Implants: Porous Sponge-Like Structure with GC Particles Crosslinked with Genipin and Stabilized with CaCl2

The homogenized fascia, sodium alginate solution, crudely fragmented fascia, ground cortical bone powder, $CaCl_2$ solution, and genipin were prepared as described in Example 1 and Example 8.

To prepare the tissue repair implant, the homogenized fascia was mixed with a sodium alginate solution and 1% genipin solution to produce a connective tissue carrier. Then the connective tissue carrier was mixed further with crudely fragmented fascia and the ground cortical bone powder. After mixing all the components, the mixture was distributed into molds with pre-determined shapes and sizes and kept in the dark for 4 to 16 hours at room temperature to allow crosslinking by genipin to occur. The structure turned dark blue after crosslinking. Then the crosslinked and molded structure was washed to remove unbound genipin, freeze-dried, treated with $CaCl_2$, washed with water, and freeze-dried again. The resultant porous sponge-like structure was then sent out for sterilization by gamma irradiation.

In one of the tissue repair implants, the porous sponge-like structure contained about 75% ground cortical particle, 2% alginate, 13% homogenized fascia, and 10% fascia fiber by dry weight. The freeze-dried, molded, tissue repair implants demonstrated high mechanical strength and maintained the shape of their mold.

Example 10

Preparation of Tissue Repair Implants: Porous Sponge-Like Structure with GC Particles Absorbed with BMP-2

The homogenized fascia, sodium alginate solution, crudely fragmented facia, ground cortical bone powder, and $CaCl_2$ solution were prepared as described in Example 1 and Example 7. Sterile recombinant human BMP-2 (rh BMP-2) produced by expressing BMP-2 gene in *E. coli* (355-BEC, R&D systems) was reconstituted in sterile 4 mM HCl containing 0.2% bovine serum albumin to a stock concentration of 0.2 µg/µL. The aliquots of rhBMP2 were stored at −10° C. to −30° C. until use.

To prepare the tissue repair implant, the homogenized fascia was mixed with a sodium alginate solution to produce a connective tissue carrier, which was mixed further with crudely fragmented fascia and the sized, freeze-dried ground cortical bone powder. After mixing all the components, the mixture was freeze-dried, treated with $CaCl_2$, washed water, and freeze-dried again. The porous sponge-like structure was then sent out for sterilization by gamma irradiation.

In one of the tissue repair implants, the porous sponge-like structure contained about 70% GC particles, 3% alginate, 11% homogenized fascia, and 16% fascia fiber by dry weight. The rh BMP-2 stock solution was added onto the freeze-dried and molded porous sponge-like structure and allowed to absorb for about 0.5 to 2 hours at room temperature. The amount of rh-BMP-2 that was absorbed on the porous sponge-like structure was about 1 micro gram to about 500 microgram per milligram of dry porous sponge-like structure. Then the structure was freeze dried again.

Example 11

Preparation of Tissue Repair Implants: Porous Sponge-Like Structure with GC Absorbed with DBM Digest The homogenized fascia, sodium alginate solution, crudely fragmented fascia, ground cortical bone powder, and $CaCl_2$ solution were prepared as described in Example 1 and Example 7. The collagenase digested DBM was prepared by digesting weighed DBM with 0.5 to 1 mg/mL collagenase. The digested DBM was centrifuged and the supernatant of the digested DBM was transferred to a new sterile tube and freeze-dried. The freeze-dried DBM collagenase digest was stored at −10° C. to −30° C. until use.

To prepare the tissue repair implant, the homogenized fascia was mixed with a sodium alginate solution to produce a connective tissue carrier, which was mixed further with crudely fragmented fascia, and the sized, freeze-dried ground cortical bone powder. After mixing all the components, the mixture was freeze-dried, treated with $CaCl_2$, washed with water, and freeze-dried again. The porous sponge-like structure was then sent out for sterilization by gamma irradiation.

In one of the tissue repair implants, the porous sponge-like structure contained about 70% GC particles, 3% alginate, 11% homogenized fascia, and 16% fascia fiber by dry weight. The lyophilized collagenase digested DBM was reconstituted with sterile normal saline, added onto the freeze-dried and molded porous sponge-like structure, and allowed to absorb for about 0.5 to 6 hours at room temperature. The amount of DBM that was absorbed on the porous sponge-like structure was about 0.1 to 100 milligram on about one milligram of dry porous sponge-like structure. Then the structure was freeze dried again.

Example 12

Characterization of the Porous Sponge-Like Structure

Tissue repair implants having a porous sponge-like structures were prepared according to the processing steps described in Example 1, Example 2, and Example 3.

Porosity and DBM distribution in the porous sponge-like structure: Various prototypes of tissue repair implants having a porous sponge-like structures containing DBM were analyzed. H&E staining of one of the representative porous sponge-like structure was shown in FIG. 1. It was found the framework of the porous sponge-like structure created by the connective tissue carrier (mixture of connective tissue homogenate and alginate, purple color) form web structures with large pores. The average pore size is larger than 100 μm. DBM particles and crudely fragmented fascia were distributed within the framework.

Hydration experiment: Each porous sponge-like structure containing DBM was cut and the dry weight of each sample was determined. Then, the sample was placed in a plastic weigh boat and 1 mL of 0.9% saline was added to each sample. The time needed for hydration was measured using a timer until the porous sponge-like structure became completely saturated and visibly changed color from white to beige. The hydrated sample was blotted lightly on a paper towel, and the wet weight was determined for each sample.

Figure 2:
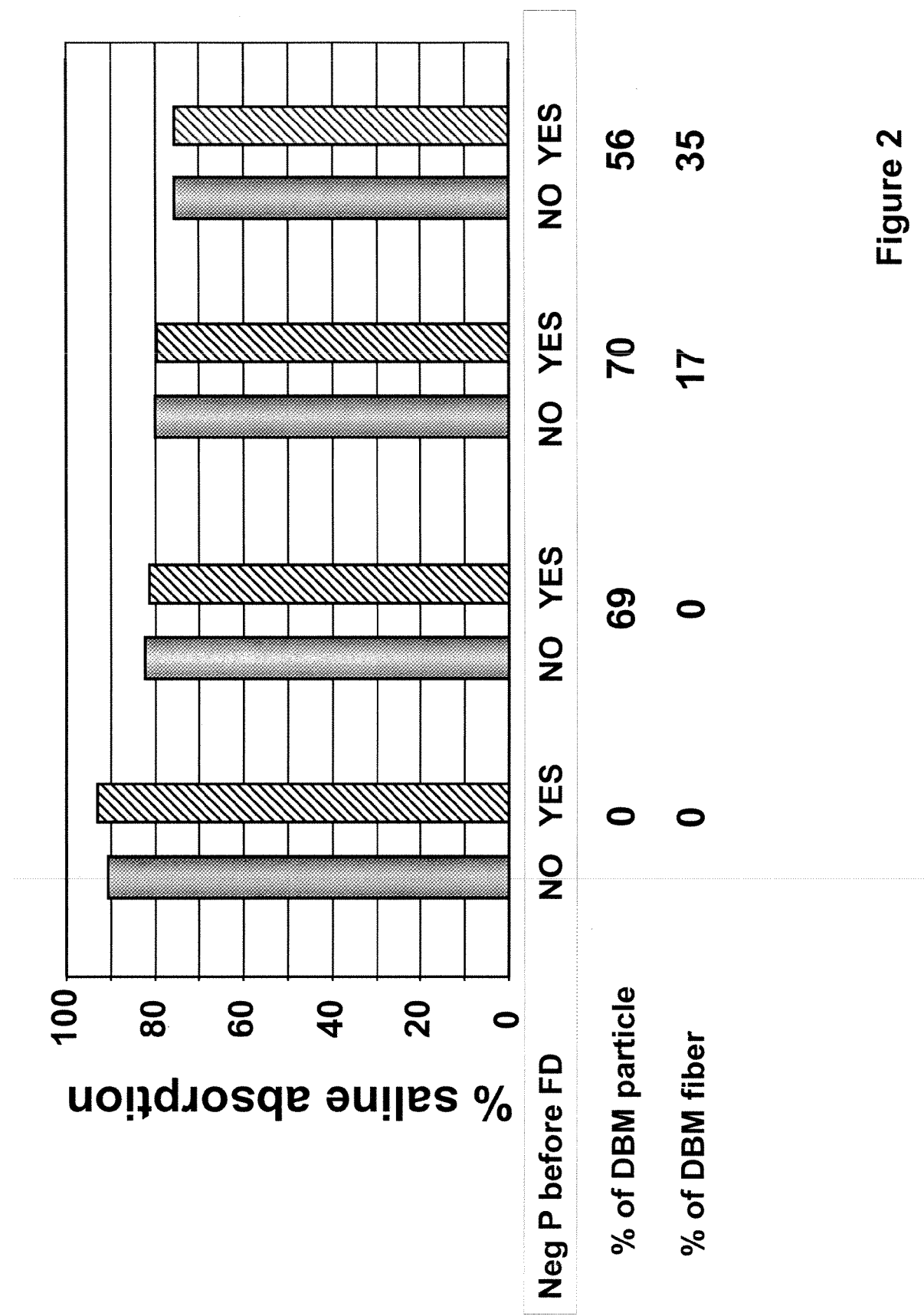
FIG. 2 shows the amount of fluid that various types of porous sponge-like structures can absorb.
Figure 3:
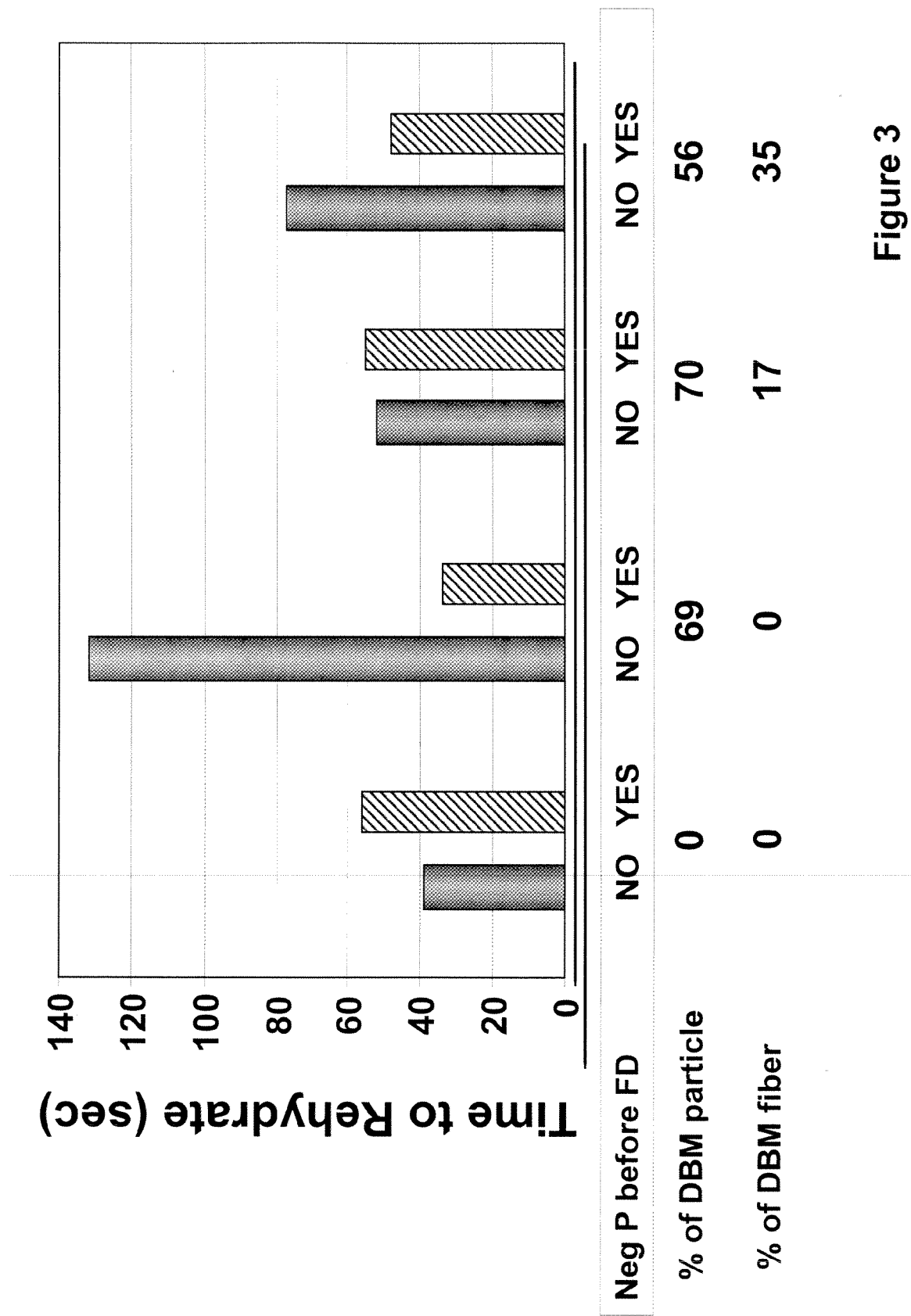
FIG. 3 shows the time required to re-hydrate various types of porous sponge-like structures.

Regardless of the application of negative hydrostatic pressure before freeze-drying, the porous sponge-like structures without DBM were able to absorb more fluid than the porous sponge-like structure containing DBM (FIG. 2). However, the amount and the type of DBM (particle or fiber) entrapped in the porous sponge-like structure did not change the amount of fluid that the porous sponge-like structure can absorb. The porous sponge-like structure containing DBM can absorb the amount of fluid that is about 80% of its wet weight or about four times of its dry weight. In addition, the application of negative hydrostatic pressure before freeze-drying tends to decrease the time required to rehydrate the porous sponge-like structure especially in the porous DBM structure containing 69% of DBM particles (FIG. 3).

Collagenase degradation assay: Three replicates of each porous sponge-like structure were weighed and placed in microcentrifuge tubes. For the samples that contained DBM, 30 mg of the porous sponge-like structure were digested with 600 micro-liters of 0.5 mg/mL collagenase in DMEM supplemented with 1% FBS. Only 10 mg of porous sponge-like structures containing no DBM were used for the collagenase degradation assay. All of the degradation samples were digested at 37° C. for 16 hours without shaking and an additional 8 hrs with shaking at 1000 r.p.m. The supernatant was separated from the pellet by centrifuging at 10000 g for 10 minutes. The pellets were freeze dried in microcentrifuge tubes, and the dry weight of each pellet was determined. Some porous sponge-like structures containing DBM that were not treated with calcium chloride were used as controls.

Figure 4:
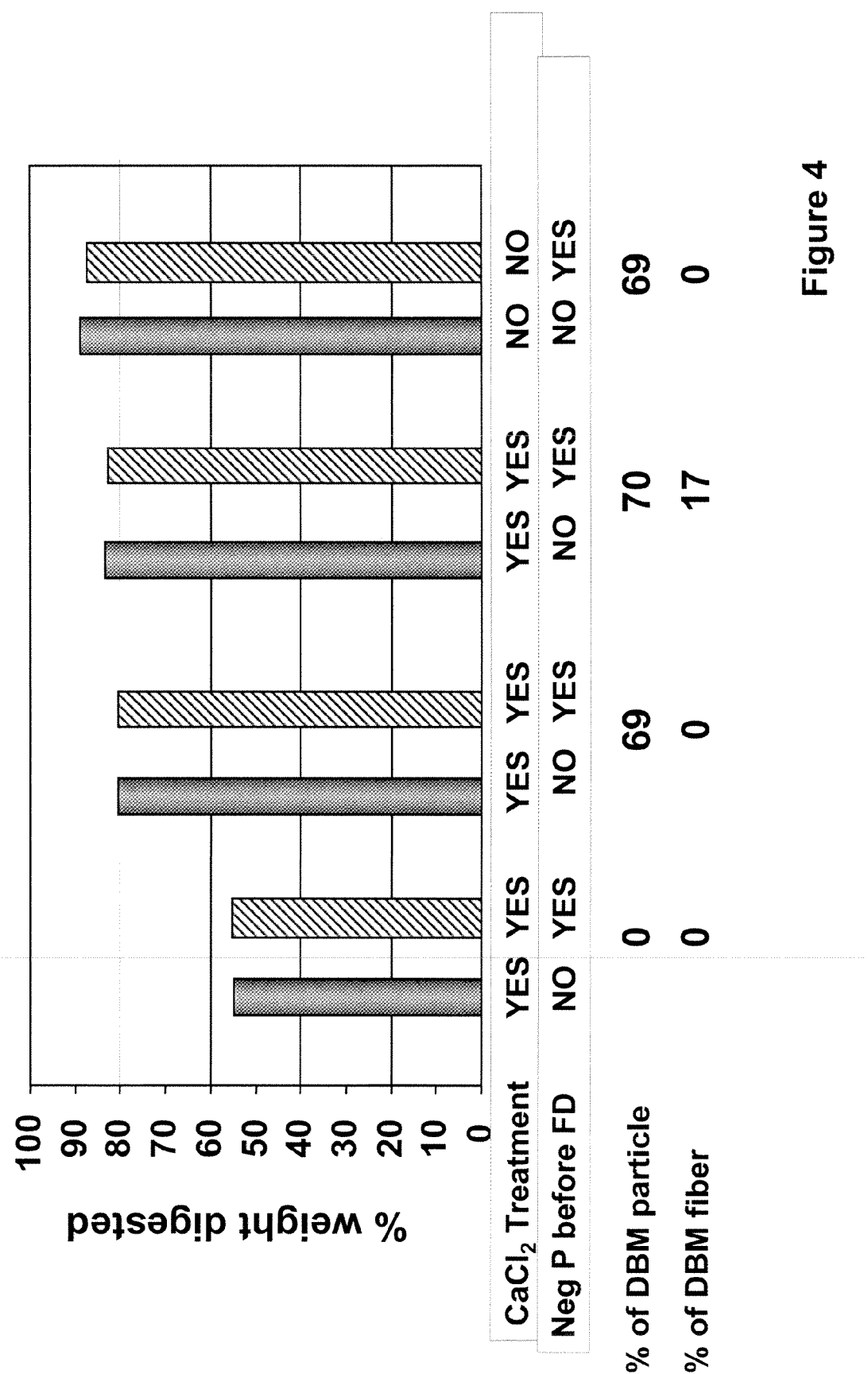
FIG. 4 shows the remaining percentage of dry weight of various types of porous sponge-like structures after 24 hours of collagenase treatment relative to the pre-treatment dry weights.

Over 50% (dry weight) of the porous sponge-like structure without DBM was digested, while over 80% of the porous sponge-like structures containing DBM were digested after 24 hrs (FIG. 4). Neither the calcium chloride treatment nor the application of negative pressure before freeze-drying changed the degradation. The amount of digested porous sponge-like structure was not different for different amount or type of DBM present within the porous sponge-like structure. Therefore, the encapsulation of the DBM in the porous sponge-like structure did not change the accessibility of the DBM.

Example 13

In vitro Biocompatibility

Figure 5:
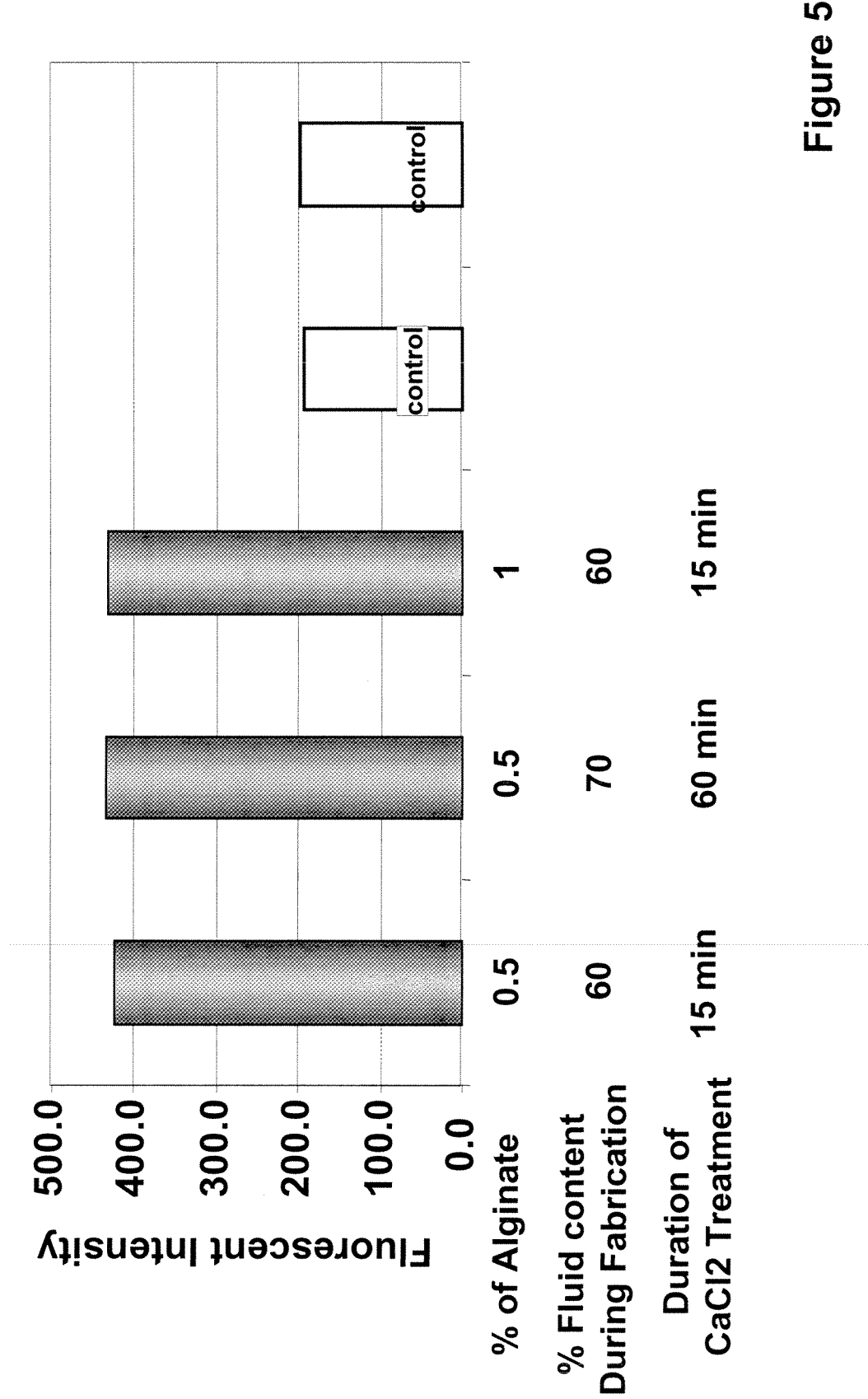
FIG. 5 shows cell viability study using alamar blue assay. Three porous sponge-like structures with DBM particles and various alginate content, fluid content, and duration of CaCl$_2$ treatment were used for the study.

Mouse fibroblast L929 cells were seeded directly on the surface of the porous sponge-like structure at the density of $0.1 \times 10^6$ cells/cm$^2$ and cultured. Cells seeded on the tissue culture plate were used as a control. Same seeding density was maintained for the porous sponge-like structure group and the control group. AlamarBlue reagent (10%) was added into the culture media on day 3 of the culture and incubated for 20 hrs. The fluorescent intensity of the culture media with AlamarBlue reagent was measured. The intensity of the fluorescence is correspondent to the viability/metabolism of the cells, i.e., the higher the intensity the more viable/metabolic active cells. As shown in FIG. 5, regardless of the concentration of alginate or the fluid content or $CaCl_2$ treatment duration, all the porous sponge-like structure tested not only maintained the cell viability but also support cell growth as the cell number in the porous sponge-like structure group was higher than that in the control groups after three day of culture. In addition, the porous sponge-like structure maintained their integrity during the culture.

Example 14

Determination of New Bone Formation

Tissue repair implants having a porous DBM structures were prepared according to the processing steps described in Example 1.

The prepared tissue repair implants and demineralized bone matrix (DBM) controls (without homogenized connective tissue or carrier) were implanted heterotopically (e.g., into muscle pouches) in the hind quarters of athymic (e.g., nude) mice.

The amounts of materials implanted were varied to always implant 20 mg of DBM. For example, 30 mg of the tissue repair implant that contains about 69% DBM composition was implanted to reach about 20 mg of DBM. Two to three mice with two implants per mouse were used for each of the tissue repair implant groups and DBM control group.

After 28 days, the implants were explanted, and one explant from each mouse was fixed. At least one histological section was cut from the center of each of these explants. Samples were fixed in 10% buffered formalin. Standard dehydration, embedding and sectioning protocols were used to produce light microscopy slides that were subsequently stained with hematoxylin and eosin. Using histomorphometric analysis, the percent new bone formed was calculated as a cross-sectional area of newly formed bone (mm$^2$) divided by the total cross-sectional area (mm$^2$) for a representative microscopic view of a histology slide multiplied by 100. Every other field of view with at least 50% bone content was used as a representative view with about 10 representative views being analyzed per slide.

Figure 6:
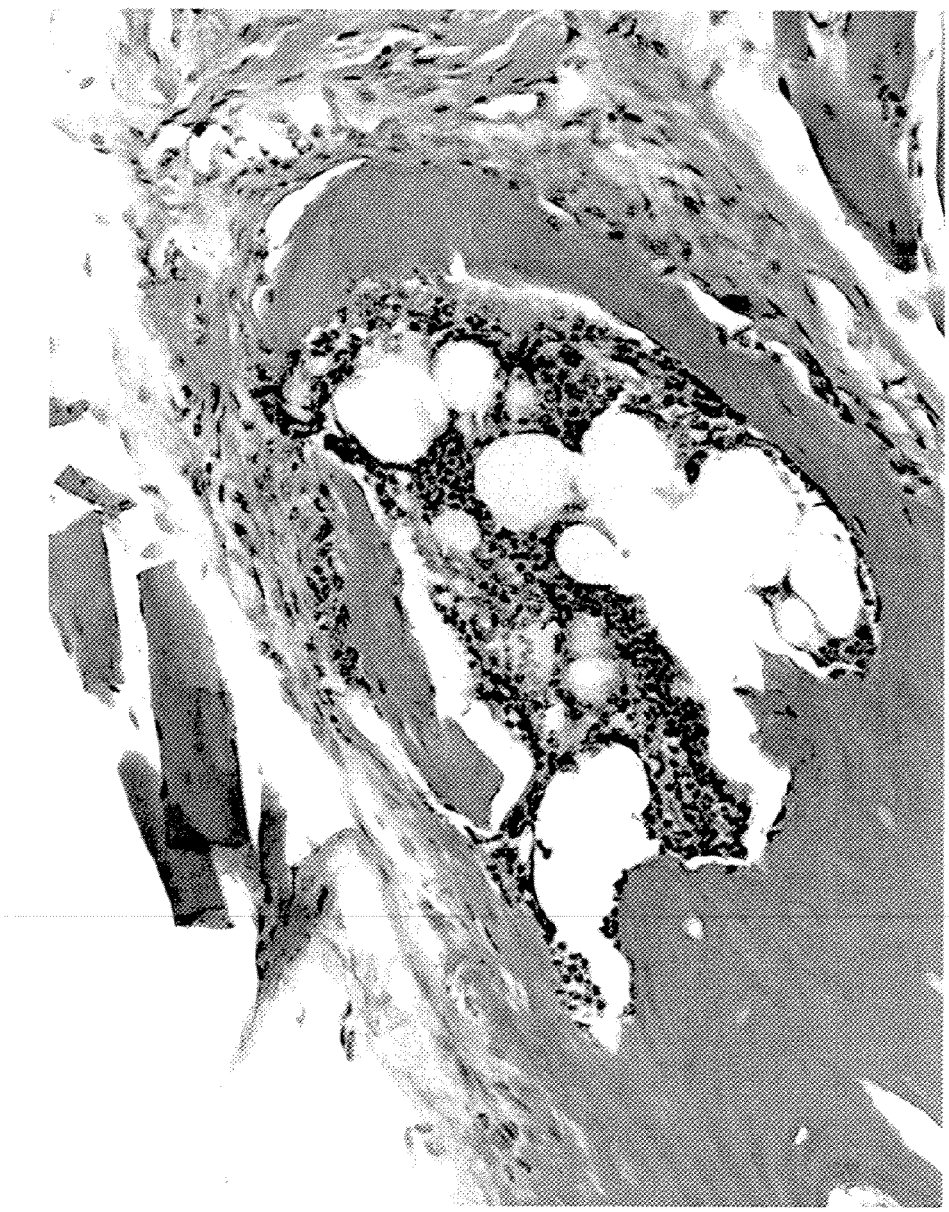
FIG. 6 shows a representative hematoxylin and eosin (H&E) staining of an explanted DBM porous sponge-like structure demonstrating new bone formation.

A representative H&E staining of an explanted porous sponge-like structure containing DBM showed new bone formation (FIG. 6). All the experimental groups and the controls had at least 9% new bone formation.

The invention claimed is:

1. A process for preparing an osteoinductive tissue repair implant having a porous sponge-like structure comprising
   a. homogenizing one or more connective tissues to produce a connective tissue homogenate;
   b. mixing said connective tissue homogenate with a solution to produce a connective tissue carrier;
   c. mixing one or more bone fragments with said connective tissue carrier to produce a tissue repair mixture;
   d. freeze-drying said tissue repair mixture to produce a porous sponge-like structure and create a three-dimensional framework to entrap said bone fragments; and
   e. treating said freeze-dried porous sponge-like structure with one or more treatment solutions to produce said osteoinductive tissue repair implant, wherein said treatment solution comprises an ionic crosslinking agent.

2. The process of claim 1, wherein a connective tissue from one or more connective tissues is mixed with said tissue repair mixture before freeze-drying.

3. A process for preparing an osteoinductive tissue repair implant having a porous sponge-like structure comprising
   a. homogenizing one or more connective tissues to produce a connective tissue homogenate;
   b. mixing said connective tissue homogenate with a solution to produce a tissue repair mixture;
   c. freeze-drying said tissue repair mixture to produce a porous sponge-like structure and create a three-dimensional framework; and
   d. treating said freeze-dried porous sponge-like structure with one or more treatment solutions to produce said osteoinductive tissue repair implant, wherein said treatment solution comprises an ionic or enzymatic crosslinking agent,
   wherein said solution comprises a bioactive supplement selected from the group consisting of fibroblast growth factor (FGF), transforming growth factor (TGF), insulin-like growth factor (IGF)-1, platelet-derived growth factor (PDGF), epidermal growth factor (EGF), vascular endothelial growth factor (VEGF), hepatocyte growth factor (HGF), parathyroid hormone-related protein (PTHrP), Indian hedgehog (Ihh), dexamethasone, insulin, transferrin, selenium, Insulin-Transferrin-Selenium (ITS), or ascorbate.

4. The process of claim 1, further comprising treating the osteoinductive tissue repair implant with a water replacing agent.

5. The process of claim 1, further comprising freeze-drying the osteoinductive tissue repair implant.

6. The process of claim 1, further comprising sterilizing the osteoinductive tissue repair implant.

7. The process of claim 1, wherein said three-dimensional framework is created by said connective tissue carrier.

8. The process of claim 1, further comprising combining said connective tissue homogenate, said connective tissue carrier, said tissue repair mixture, said porous sponge-like structure, or said osteoinductive tissue repair implant with one or more agents selected from the group consisting of growth factors, differentiation factors, cytokines, and anti-inflammatory agents.

9. A method of repairing defects in bone, cartilage, or soft tissue comprising
   implanting the osteoinductive tissue repair implant prepared by the process of claim 1 at the site of defect.

10. An osteoinductive tissue repair implant having a porous sponge-like structure prepared by the process of claim 1, wherein the pore size is larger than about 50 microns.

11. An osteoinductive tissue repair implant having a porous sponge-like structure prepared by the process of claim 1, wherein the void volume is from about 10% to about 95%.

12. An osteoinductive tissue repair implant having a porous sponge-like structure prepared by the process of claim 1, wherein the void volume is from about 30% to about 80%.

13. The process of claim 1, wherein said osteoinductive tissue repair implant having a porous sponge-like structure is in the form of rod, sheet, cube, tube, particle, sphere, ellipsoid, wedge, or ribbon.

14. The process of claim 1, wherein said connective tissue homogenate is made from one more connective tissue(s) of human origins.

15. The process of claim 1, wherein said connective tissue is obtained from fascia, cartilage, tendon, ligament, pericardium, fat, urethra, small intestine, dermis, bone or a mixture of two or more of the above.

16. The process of claim 1, wherein said connective tissue in the connective tissue homogenate is cleaned and disinfected.

17. The process of claim 15, wherein said connective tissue is devitalized to remove cellular components.

18. The process of claim 16, wherein said connective tissue is freeze-dried.

19. The process of claim 1, wherein producing said connective tissue homogenate is carried out by homogenizing said connective tissue at a temperature from about 15° C. to about 100° C. for a period of time of about 0.5 minutes to about 30 minutes.

20. The process of claim 19, wherein said connective tissue is homogenized in solution.

21. The process of claim 1, wherein the weight percentage of said connective tissue homogenate in said osteoinductive tissue repair implant is no more than 80% in the dry state.

22. The process of claim 1, wherein the weight percentage of said connective tissue homogenate in said osteoinductive tissue repair implant is no more than 50% in the dry state.

23. The process of claim 1, wherein the weight percentage of said connective tissue homogenate in said osteoinductive tissue repair implant is no more than 20% in the dry state.

24. The process of claim 1, wherein said solution in step b comprises one or more polysaccharides selected from the group consisting of alginate, propylene glycol alginate, native or crosslinked chitosan, starch, cellulose and its derivatives, xanthan gum, dextran, carrageenan, hyaluronic acid, condroitin sulfate, locust bean gum, gum tragacanth, gum arabic, curdlan, pullulan, scleroglucan, or lower methoxylpectin.

25. The process of claim 1, wherein said solution in step b comprises (i) salts of calcium, barium, aluminum, strontium, copper, zinc, magnesium, manganese, cobalt, or iron; or (ii) glutaraldehyde, glyceraldehyde, genipin, glucose or ribose, poly(ethylene glycol) diepoxide crosslinker, poly(ethylene glycol) diglycidyl ether, ethyl(dimethylaminopropyl) carbodiimide (EDC) and N-hydroxysuccinimide (NHS), transglutaminase, ethylenediamine, lysyl oxidase, hexamethylene diisocyanate (HMDIC); dimethyl suberimidate (DMS), dimethyl-3-3'-dithiobispropionimidate (DTBP), or acryl azide.

26. The process of claim 1, wherein said solution in step b comprises a material selected from the group consisting of collagen, gelatin, agarose, hyaluronic acid, fibrin, chitin, biotin, avidin, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, hyaluronan, alginate, polyurethane, polylactic acid, or a combination comprising at least one of the foregoing polymers.

27. The process of claim 1, wherein said solution in step b comprises a bioactive supplement selected from the group consisting of fibroblast growth factor (FGF), transforming growth factor (TGF), insulin-like growth factor (IGF)-1, platelet-derived growth factor (PDGF), epidermal growth factor (EGF), vascular endothelial growth factor (VEGF), hepatocyte growth factor (HGF), parathyroid hormone-related protein (PTHrP), Indian hedgehog (Ihh), dexamethasone, insulin, transferrin, selenium, Insulin-Transferrin-Selenium (ITS), or ascorbate.

28. The process of claim 1, wherein said solution in step b comprises a bioactive supplement selected from the group consisting of cytokine of granulocyte/macrophage colony stimulating factor (GM-CSF), granulocyte colony-stimulating factor (G-CSF), tumor necrosis factor (TNF)-α, interleukin (IL)-1β, IL-4, IL-6, IL-8, IL-10, secretory leukocyte protease inhibitor (SLPI), monocyte chemotactic protein-1 (MCP1), macrophage inflammatory protein (MIP)-1α, MIP-2, IL-18, angiopoietin, keratinocyte Growth Factor (KGF), endothelin, interferon regulatory factor (IFN)-α, or IFN-β.

29. The process of claim 1, wherein said solution in step b comprises a bioactive supplement selected from the group consisting of anti-inflammatory agent of an IL-1αR antibody, TNF-α receptor antagonist, cyclooxygenase-2 specific inhibitors, mitogen-activated protein (MAP) kinase inhibitors, NO synthase inhibitors, nuclear factor (NF)-κB inhibitors, or inhibitors of matrix metalloproteineasse (MMP).

30. The process of claim 29, wherein said bioactive supplement is extracted from tissue selected from the group consisting of demineralized bone matrix, basement membrane, or submucosa matrix.

31. The process of claim 1, wherein said solution in step b comprises an antioxidant selected from the group consisting of sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene.

32. The process of claim 1, wherein said solution in step b comprises a photoactive agent selected from the group consisting of a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide, N,N9-bis(3-diazopyruvoyl)-2,29-(ethylenedioxy)bis-(ethylamine) (DPD); diazopyruvoyl (DAP); methylene blue, erythrosin, phloxime, thionine, methylene green, rose Bengal, acridine orange, xanthine dye, and thioxanthine dyes, ethyl eosin, eosin Y, or a combination comprising at least one of the foregoing photoactive agents.

33. The process according to 32, wherein said photoactive agent is activated by UV light or a laser.

34. The process of claim 24, wherein the weight percentage of said polysaccharides in said osteoinductive tissue repair implant is no more than 20% in the dry state.

35. The process of claim 24, wherein the weight percentage of said polysaccharides in said osteoinductive tissue repair implant is no more than 5% in the dry state.

36. The process of claim 1, wherein said bone fragments comprise non-demineralized bone, partially demineralized bone, demineralized bone, ceramics, hydroxyapatite, calcium phosphate, calcium sulfate, calcium carbonate, or a combination of two or more of the above.

37. The process of claim 1, said bone fragments are from human or animals.

38. The process of claim 1, wherein said bone fragments are in the form of particles, fibers, rods, or cubes.

39. The process of claim 38, wherein said particles have an average particle size of about 125 micron to about 2000 micron.

40. The process of claim 38, wherein said fibers have an average width of 0.1 to 2 mm and an average length of about 0.3 mm to about 100 mm.

41. The process of claim 38, wherein said rods have average width of 0.5 to 5 mm and an average length of about 1 mm to about 100 mm.

42. The process of claim 38, wherein said cubes have an average volume of about 0.001 mm$^3$ to an average volume of about 1000 mm$^3$.

43. The process of claim 36, wherein said demineralized bone has a residual calcium content from about 1% to about 4%.

44. The process of claim 1, wherein the weight percentage of said bone fragments in said osteoinductive tissue repair implant is about 0.1% to about 95% in the dry state.

45. The process of claim 1, wherein the weight percentage of said bone fragments in said osteoinductive tissue repair implant is about 10% to about 90% in the dry state.

46. The process of claim 1, wherein the weight percentage of said bone fragments in said osteoinductive tissue repair implant is about 30% to about 80% in the dry state.

47. The process of claim 1, wherein said tissue repair mixture is placed in a mold before said freeze-drying step.

48. The process of claim 1, wherein said tissue repair mixture is processed under negative hydrostatic pressure before freeze-drying.

49. The process of claim 1, further comprising treating said freeze-dried porous sponge-like structure with an additional treatment solution comprising chemical crosslinking agents; or photoactive agents.

50. The process of claim 1, wherein said ionic crosslinking agent comprise one or more metal ions selected from the group consisting of calcium, barium, aluminum, strontium, copper, zinc, magnesium, manganese, cobalt, or iron.

51. The process of claim 3, wherein said treatment solution comprises transglutaminase or lysyl oxidas.

52. The process of claim 49, wherein said chemical crosslinking agents comprise glutaraldehyde, glyceraldehyde, genipin, glucose, ribose, poly(ethylene glycol)diepoxide, poly(ethylene glycol)diglycidyl ether, EDC and NHS, or acryl azide.

53. The process of claim 1, wherein said treatment solution comprises a material selected from the group consisting of collagen, gelatin, agarose, modified hyaluronic acid, fibrin, chitin, biotin, avidin, demineralized bone matrix, proteoglycans, laminin, fibronectin, elastin, heparin, glycerol, sucrose octasulfate, polyethylene glycol, polymethylmethacrylate, polyurethane, acryloilmorpholine, N,N-dimethyl acrylamide, N-vinyl pyrrolidone and tetrahydrofurfuryl methacrylate, hydroxyapatite, hyaluronan, alginate, polyurethane, polylactic acid, or a combination comprising at least one of the foregoing materials.

54. The process of claim 8, wherein said one or more agents is incorporated in the treatment solution.

55. The process of claim 1, wherein said treatment solution comprises antioxidants.

56. The process of claim 1, wherein said treating step comprises treating said freeze-dried porous sponge-like structure with more than one treatment solutions simultaneously or sequentially to stabilize the porous sponge-like structure and further entrap said bone fragments.

57. The process of claim 1, wherein said treating step is carried out for a duration of about 5 minutes to about 16 hours.

58. The process of claim 1, wherein said treating step is carried out for a duration of about 15 minutes to about 120 minutes.

59. The process of claim 1, wherein said treating step is carried out for a duration of about 30 minutes to about 60 minutes.

60. The process of claim 6, wherein said sterilization is carried out using gamma irradiation, super critical solution, ethylene oxide, or electronic-beam.

61. A process for repairing a defect comprising implanting said osteoinductive tissue repair implant having a porous sponge-like structure according to claim 1 or 3 into a defect without rehydration to allow said osteoinductive tissue repair implant to absorb blood or fluid as well as autologous cells in situ.

62. A process for repairing a defect comprising rehydrating said osteoinductive tissue repair implant having a porous sponge-like structure according to claim 1 or 3 with a rehydrating solution; optionally seeding vital cells on said osteoinductive tissue repair implant to render said osteoinductive tissue repair implant vital; optionally culture said cell-seeded osteoinductive tissue repair implant before implantation; implanting said osteoinductive tissue repair implant into said defect.

63. The process of claim 62, wherein said rehydrating solution comprises blood or bone marrow aspirate, platelet rich plasma, enzymes, bioactive supplements, natural polymers, synthetic polymers, photoactive agents, antioxidants, crosslinking agents, antimicrobial agents, vital cells, one or more agents that have bioactive supplement binding site(s), or a mixture of two or more of the above.

64. The process of claim 62, wherein said vital cells comprise one or more than one type of cells from autologous or allograft bone marrow aspirate; stromal cells from bone marrow, stromal cells from fat, synovium, periostieum, perichondrium, muscle, dermis, umbilical cord blood, and Warton's jelly; or pericytes.

65. The process of claim 1 or 3, wherein said solution in step b comprises alginate.

66. The process of claim 1 or 3, further comprising cutting the one or more connective tissues prior to the homogenizing, wherein at least a part of the cut connective tissues is homogenized in step a.

67. The process of claim 1 or 3, wherein the treating is performed for a time period of 5 to 120 minutes.

* * * * *